(12) United States Patent
Zhang et al.

(10) Patent No.: US 9,017,962 B2
(45) Date of Patent: Apr. 28, 2015

(54) INTRACELLULAR REPORTERS

(75) Inventors: Jin Zhang, Baltimore, MD (US); Robert Howard Newman, Baltimore, MD (US); Xinxin Gao, Baltimore, MD (US); Michael David Allen, Baltimore, MD (US); Matthew David Fosbrink, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 537 days.

(21) Appl. No.: 12/674,008

(22) PCT Filed: Aug. 20, 2008

(86) PCT No.: PCT/US2008/073672
§ 371 (c)(1),
(2), (4) Date: Mar. 31, 2010

(87) PCT Pub. No.: WO2009/026338
PCT Pub. Date: Feb. 26, 2009

(65) Prior Publication Data
US 2010/0202970 A1  Aug. 12, 2010

Related U.S. Application Data

(60) Provisional application No. 60/965,628, filed on Aug. 20, 2007, provisional application No. 60/965,610, filed on Aug. 21, 2007, provisional application No. 60/965,635, filed on Aug. 21, 2007.

(51) Int. Cl.
| | | |
|---|---|---|
| *C12Q 1/42* | (2006.01) | |
| *C07K 1/00* | (2006.01) | |
| *C12N 15/62* | (2006.01) | |
| *C12Q 1/48* | (2006.01) | |
| *G01N 33/542* | (2006.01) | |

(52) U.S. Cl.
CPC ............ *C12N 15/62* (2013.01); *C07K 2319/61* (2013.01); *C12Q 1/42* (2013.01); *C12Q 1/485* (2013.01); *G01N 33/542* (2013.01); *G01N 2333/9121* (2013.01); *G01N 2333/916* (2013.01)

(58) Field of Classification Search
USPC ..................................... 435/7.1, 21; 530/350
See application file for complete search history.

(56) References Cited

U.S. PATENT DOCUMENTS

| | | |
|---|---|---|
| 2005/0153310 A1 | 7/2005 | Fan |
| 2005/0260593 A1 | 11/2005 | Kumar |
| 2006/0160108 A1 | 7/2006 | Romanov |
| 2006/0292652 A1 | 12/2006 | Curtis |
| 2007/0111270 A1 | 5/2007 | Zhang |

OTHER PUBLICATIONS

Luo et al., "Interaction of calcineurin with a domain of the transcription factor NFAT1 that controls nuclear import", Proc. Natl. Acad. Sci. USA 93, pp. 8907-8912, Aug. 10, 1996.
Newman & Zhang, "Visualization of phosphatase activity in living cells with a FRET-based calcineurin activity sensor," Mol. BioSyst. 4, 496-501, 2008.
Hires et al., "Optical measurement of synaptic glutamate spillover and reuptake by linker optimized glutamate-sensitive fluorescent reporters," Proc Natl Acad Sci U S A. Mar. 18, 2008;105(11):4411-6. Epub Mar. 10, 2008.
Nikolaev et al., "Novel single chain cAMP sensors for receptor-induced signal propagation," J Biol Chem. Sep. 3, 2004;279(36):37215-8. Epub Jul. 1, 2004.
Van Roessel et al., "Imaging into the future: visualizing gene expression and protein interactions with fluorescent proteins," Nat Cell Biol. Jan. 2002;4(1):E15-20.

*Primary Examiner* — Maryam Monshipouri
(74) *Attorney, Agent, or Firm* — Banner & Witcoff, Ltd.

(57) ABSTRACT

The invention provides a variety of molecular tools for use in live-cell tracking of activities of biomolecules and in high-throughput drug screening.

23 Claims, 25 Drawing Sheets

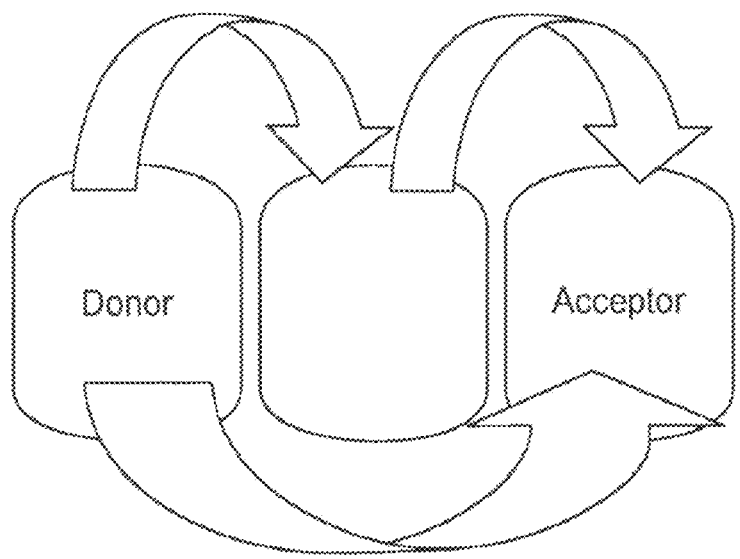
FIG. 1
| Cerulean | FHA1 | LRRATLVD | mCherry | mVenus | CRY AKAR
FIG. 2A
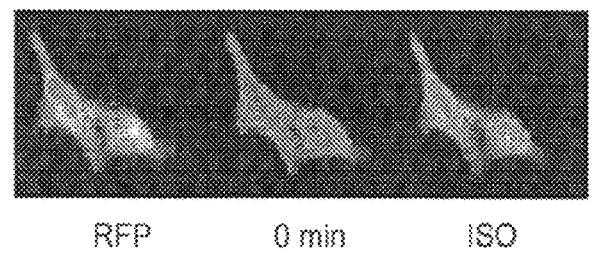
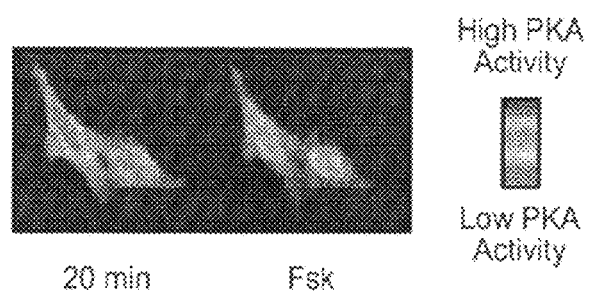
FIG. 2B FIG. 3A
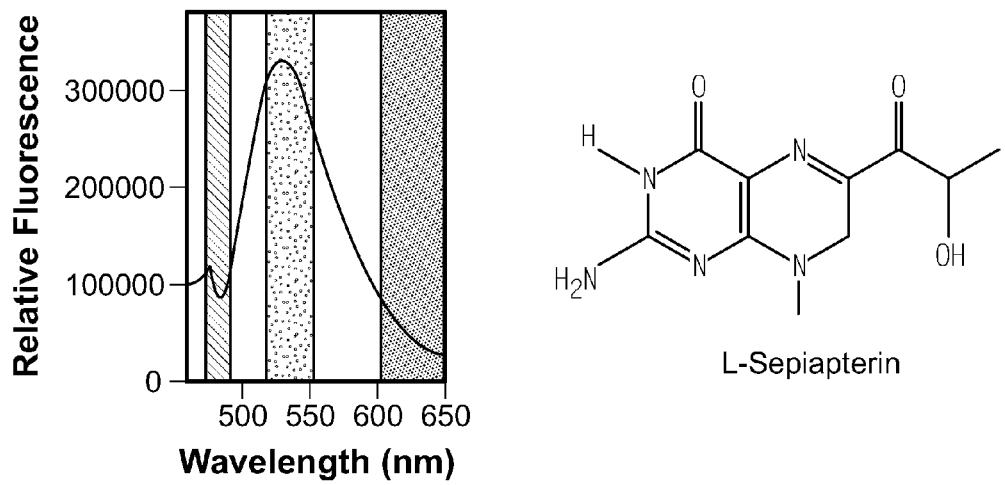
FIG. 3B
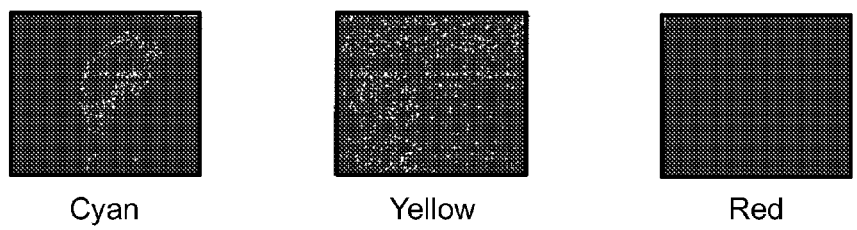
Cyan     Yellow     Red
FIG. 4A
| mCherry | mVenus | FHA1 | LRRATLVD | Cerulean | RYC AKAR
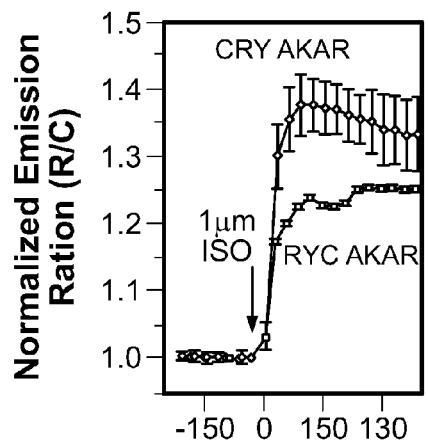
FIG. 4B

INTRACELLULAR REPORTERS

This application is a national phase application of PCT/US2008/073672 which was filed on Aug. 20, 2008 and published in English on Feb. 26, 2009. PCT/US2008/073672 claims the benefit of and incorporates by reference provisional application Ser. No. 60/965,628 filed Aug. 20, 2007; Ser. No. 60/965,610 filed Aug. 21, 2007; and Ser. No. 60/965,635 filed Aug. 21, 2007.

This application incorporates by reference the contents of a 17.7 kb text file created on Apr. 16, 2013 and named "12674008substitutesequencelisting.txt," which is the sequence listing for this application.

Inventions described herein were made with the support of NIH Grants DK073368 and R21 CA122673. The U.S. government therefore has certain rights in the inventions.

FIELD OF THE INVENTION

The invention relates to reporters for intracellular enzymatic activities.

BACKGROUND OF THE INVENTION

Many genetically encodable reporters have been developed to monitor spatio-temporal dynamics of specific enzymes in living cells. However, improved reporters are desired. For example, the Akt reporter "Aktus" (Sasaki et al., *J. Biol. Chem.* 278, 30945-51, 2003), requires overexpression of Akt to show signals in CHO cells, decreasing its applicability to study the regulation mechanism of endogenous Akt. The sensitivity of the Akt activity reporter "B Kinase Activity Reporter" (BKAR) (Kunkel et al., *J. Biol. Chem.* 280, 5581-87, 2005) is improved relative to Aktus, but its signal amplitude still limits its biological applications.

In addition, the art does not yet have enzymatic reporters for some enzymes. For example, there are no reliable methods available for measuring activity dynamics of JNK, one of the mitogen activated protein kinases (MAPKs), within subcellular compartments with high spatiotemporal resolution in living cells. Similarly, phosphatase activity reporters have not been described.

Thus, there is a continuing need in the art for sensitive and specific enzyme reporters, particularly genetically encodable reporters, which can be used to measure enzyme activities with high spatial and temporal resolution in vivo.

BRIEF DESCRIPTION OF THE DRAWINGS

FIG. 1. An embodiment of a tunable FRET reporter. Donor and acceptor fluorophores undergo energy transfer in a tunable FRET circuit via two paths: direct and sequential. The direct path is represented by the lower arrow, showing the donor transfers energy to the acceptor. The sequential path is made possible by an intermediate fluorophore, a "tuner." Energy is passed from donor to the tuner and from the tuner to the acceptor. By adjusting the spectral properties of the tuner, the efficiency of this FRET circuit can be altered. LRRATLVD, amino acids 108 of SEQ ID NO:18.

FIG. 2A-C. Development of a PKA reporter with a tunable FRET circuit. FIG. 2A, domain structures of "CRY AKAR." FIG. 2B, RFP fluorescence image and time course of two HeLa cells expressing CRY AKAR treated with isoproterenol (ISO) and forskolin (Fsk). FIG. 2C, representative time course of HeLa cells expressing CRY AKAR treated with ISO followed by treatment with Fsk.

FIG. 3A-B. Cyan-red ratiometric readout of CRY AKAR allows simultaneous use of a yellow fluorescent compound L-sepiapterin, which cannot be used with the common CFP-YFP FRET pair. FIG. 3A, Emission spectrum of L-sepiapterin with excitation at 434 nm. FIG. 3B, Individual fluorescence images of CRY AKAR reflecting cyan, yellow, and red emission with CFP excitation in the presence of the fluorescent compound L-sepiapterin.

FIG. 4A-B. CRY AKAR compared with a variant, RYC AKAR. FIG. 4A, domain structure of RYC AKAR in which the positions of the fluorophores in the AKAR chimera have been rearranged. FIG. 4B, time courses of red over cyan emission ratio changes for RYC AKAR and CRY AKAR in HeLa cells treated with ISO. The average responses of AKAR RYC were 25.9%±7.1% (n=2) and 38.1%±3.4% (n=4) for the agonists ISO and Fsk respectively.

FIG. 9A, reporters comprising each of three Akt phosphorylation motifs, with a linker region on each side. "FOXO1" (forkhead box transcription factor 1), SEQ ID NO:14; "BAD," SEQ ID NO:15; and an optimal peptide sequence, SEQ ID NO:16. FIG. 9B, reporters comprising the Akt phosphorylation motif of FOXO1 as the substrate region, FHA1 as the binding partner, and different variants of cyan and yellow fluorescent proteins (Cerulean, cpV K156, cpV E172, cpVL194, cpV A228 [circularly-permutated versions of the yellow fluorescent protein variant, Venus] and YPet). FIG. 9C, Representative responses of different versions of AktAR. NIH3T3 cells were transfected with AktAR constructs then serum starved for 24 hours. The ratio of yellow emission to cyan emission was recorded over time. PDGF (50 ng/ml) was added at the zero time point.

FIG. 10A, Monitoring Akt activity with AktAR. AktAR was overexpressed in serum-starved NIH3T3 cells, with or without co-expression of Akt1. Response of an AktAR-T/A mutant (where the threonine in the substrate motif was mutated to an alanine) upon stimulation of PDGF was also showed. FIG. 10B, AktAR revealing balance between Akt and phosphatase activity. NIH3T3 cells overexpressing AktAR were serum-starved then stimulated with 50 ng/ml PDGF, followed by addition of 5 nM Calyculin A.

FIG. 11A, AktAR insensitive to PKC activation. NIH3T3 cells overexpressing AktAR were serum-starved then stimulated with 50 ng/ml PMA to activate PKC at the zero time point, followed by addition of 50 ng/ml PDGF. FIG. 11B, AktAR insensitive to PKA activation. NIH3T3 cells overexpressing AktAR were serum-starved then stimulated with 50 µM forskolin to activate PKA at the zero time point. FIG. 11C, Reversibility of AktAR. Serum-starved NIH3T3 cells overexpressing AktAR were treated with 50 ng/ml PDGF then 20 µM LY294002. FIG. 11D, AktAR specifically detecting Akt activity. Serum-starved NIH3T3 cells overexpressing AktAR were pre-incubated with either 6 µM SH-5 in HBSS buffer or HBSS buffer alone then stimulated with 50 ng/ml PDGF. FIG. 11E, AktAR reporting Akt activity in un-starved NIH3T3 cells. NIH3T3 cells overexpressing either AktAR or BKAR were stimulated with 50 ng/ml PDGF.

FIG. 12A, Localization of Mito-AktAR. AktAR was targeted to the mitochondrial outer membrane by an N-terminal DAKAP1a motif. MitoTracker staining confirmed localization of Mito-AktAR to the mitochondrial outer membrane. FIG. 12B, graph demonstrating that AktAR detects Akt activity at the mitochondrial outer membrane. Mito-AktAR was overexpressed in serum-starved NIH3T3 cells with or without overexpressed mCherry-Akt1 or Mito-mCherry-Akt1. PDGF was added at the zero time point. For cells overexpressing Mito-AktAR and mCherry-Akt1, 20 µM LY294002 was added 15 min after PDGF addition. FIG. 12C, graph demonstrating that AktAR reveals a balance between Akt and phosphatase activity at the mitochondrial outer membrane. Mito-AktAR was overexpressed in serum-starved NIH3T3 cells with or without overexpressed mCherry-Akt1 or Mito-mCherry-Akt1. PDGF was added at the zero time point, followed by addition of 5 nM Calyculin A.

FIG. 13A, Localization of plasma membrane targeted AktAR. AktAR was targeted to the plasma membrane by addition of either the N-terminal portion of Lyn kinase gene at the 5' end or the CAAX tag at the 3' end of AktAR sequence. C stands for a cysteine, A for aliphatic amino acids, and X for any amino acid. FIG. 13B, graph demonstrating Akt activity varying at different plasma membrane microdomains. Serum-starved NIH3T3 cells overexpressing plasma membrane targeted constructs, PM(Lyn)-AktAR or AktAR-PM(CAAX), were treated with 50 ng/ml PDGF. FIG. 13C, graph demonstrating that membrane cholesterol depletion diminishes Akt activity at the plasma membrane lipid rafts. Serum-starved NIH3T3 cells overexpressing either PM(Lyn)-AktAR or AktAR-PM (CAAX) were pre-incubated with 5 mM MβCD for 30 min, then stimulated with PDGF.

FIG. 15A, HeLa cells were transfected with the reporter and imaged 24 h later in HBSS containing 10% FBS on stage warmer heated to 37° C. The reporter was evenly distributed throughout the nucleus and cytoplasm. FIG. 15B, graph demonstrating response of reporter to anisomycin. HeLa cells were transfected with the reporter and imaged 24 h later. The transfected cells were treated with 5 µM anisomycin on stage and imaged. Anisomycin induced an increase in emission ratio with a maximum of ~30%. FIG. 15C, graph demonstrating response of reporter to FBS. Transfected HeLa cells were treated with 10% FBS on stage. FBS induced a ~15% change in emission ratio and addition of 5 µM anisomycin led to a further increase in emission ratio up to ~30%.

FIG. 16A, Co-transfection of reporter with mCherry-JIPδ. To inhibit JNK activity, HeLa cells were co-transfected with the reporter and mCherry-JIPδ and imaged 24 h later in HBSS containing 10% FBS on stage warmer heated to 37° C. Co-transfection of mCherry-JIPδ led to a significant decrease in emission ratio with delayed kinetics strongly suggesting that the reporter is specific to JNK activity. FIG. 16B, Response of reporter to inhibition of p38 MAPK. HeLa cells were pre-treated with 25 µM SB203580 for 45 min then imaged in the continual presence of 25 µM SB203580. Inhibiting p38 MAPK does not affect the response of the reporter.

FIG. 20A demonstrates that the subcellular distribution of NFAT1 is regulated by the phosphorylation state of its N-terminal regulatory domain. A rise in intracellular calcium ion concentration, $[Ca^{2+}]_i$, activates calmodulin (CaM), thereby stimulating calcineurin (CaN) activity. Once activated, calcineurin catalyzes dephosphorylation of the regulatory domain of NFAT1 leading to its translocation into the nucleus where it drives the expression of target genes. For simplicity, only the regulatory domain is shown. Several regulatory elements contained within the regulatory domain of NFAT1 also are highlighted. Light gray boxes, casein kinase 1α (CK1α) and calcineurin docking sites; black box, nuclear localization signal (NLS) composed of basic amino acid residues; dark gray boxes, highly-conserved serine-rich motifs found in all canonical NFAT family members (SRR, serine-rich region; SP, SPxx motif). Sites of phosphorylation are depicted as circles, while those dephosphorylated by calcineurin are marked by an "x. " FIG. 20B, domain structure of a calcineurin activity reporter. A region of the regulatory domain of NFAT1, ranging from amino acid residue 1 to n, is sandwiched between the FRET pair, ECFP and cpV(L194). Restriction sites used for cloning are shown.

FIG. 23A, graph of average response of CaNAR1 in the presence (black squares) or absence (gray diamonds) of cyclosporin A (CsA, 1-µM, 10 minute preincubation). Ionomycin and $CaCl_2$ treatments are as described for FIG. 22. The standard error at each time point is shown (n=4 and 6 in the presence or absence of CsA, respectively). FIG. 23B, the electrophoretic mobility of CaNAR1 isolated from HeLa cell lysates was determined at various times after ionomycin addition using standard western blotting techniques using a rabbit anti-GFP antibody (diluted 1:4000 in blocking buffer) was used to probe for CaNAR1.

DETAILED DESCRIPTION

Figure 2C:
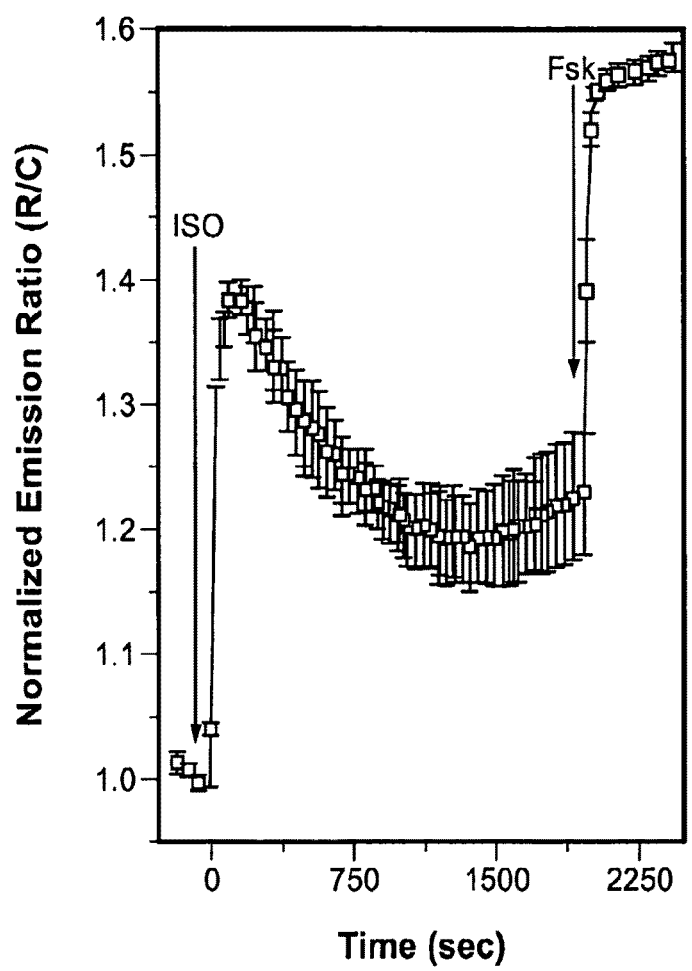
Figure 5:
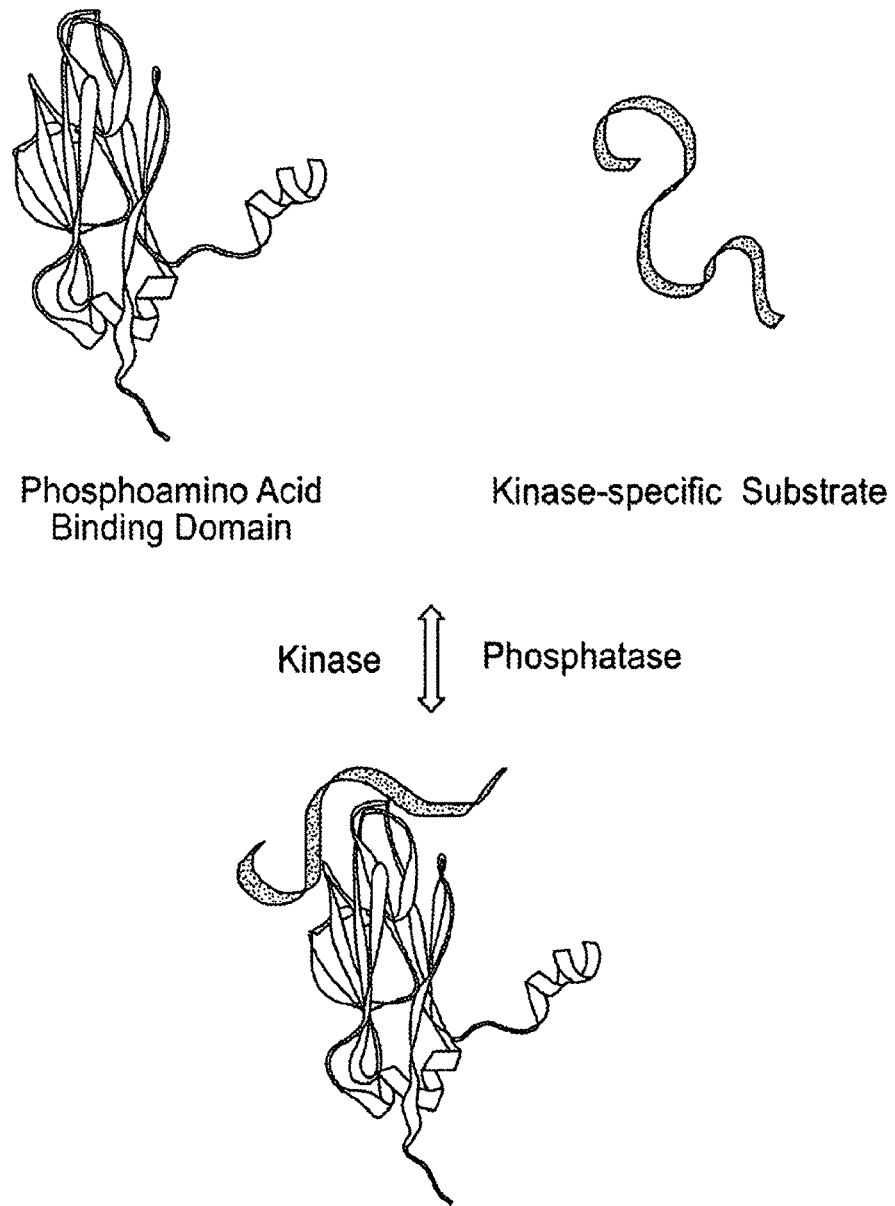
FIG. 5. Cartoon showing an embodiment of a bimolecular reporter (Bimolecular Indicator Reporter, BindR). This BindR is a simple, kinase-inducible switch containing two polypeptides: a phosphoamino acid binding domain (PAABD) and a kinase substrate. Upon phosphorylation of the substrate by the kinase of interest, the PAABD will bind it and change its conformation, generating a FRET response.
Figure 6:
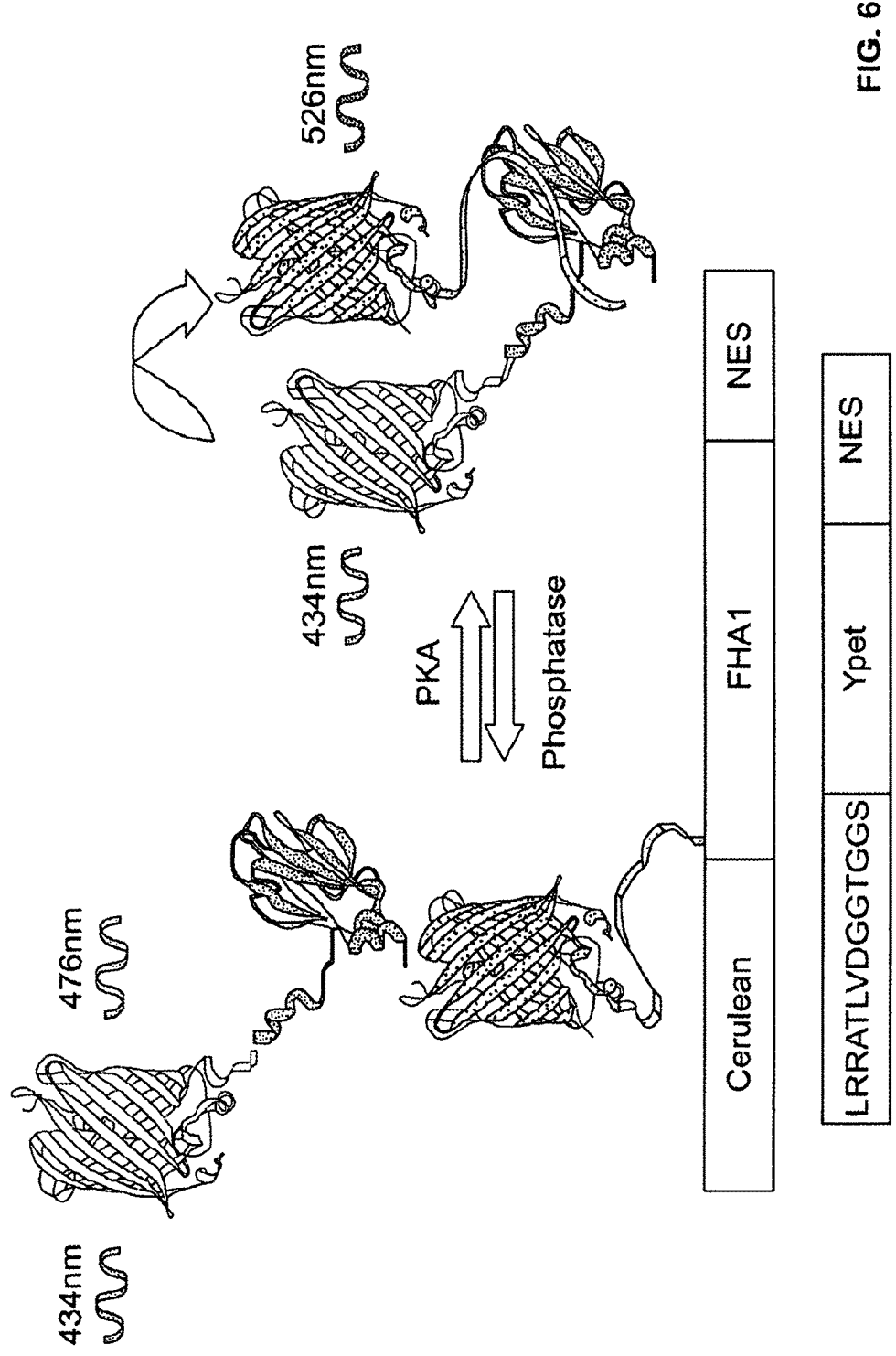
FIG. 6. Cartoons and domain structures of a PKA BindR. The forkhead associated domain 1 (FHA1) of the yeast protein Rad53 is used as the PAABD in this BindR embodiment. The substrate is a modified Kemptide containing a consensus phosphorylation site for Protein Kinase A (PKA). LRRATLVDGGTGGS, amino acids 1-14 of SEQ ID NO:18.

The invention provides genetically encoded reporters which can be used to measure intracellular enzymatic activity. The reporters are useful, inter alia, for high throughput drug screening and to monitor enzymatic activity in various disease states.

"Tunable RET"

Genetically encoded reporters based on fluorescence resonance energy transfer (FRET) have become powerful tools for monitoring cellular events in living systems. Typically required for engineering such reporters are two fluorophores with spectra within the constraints of a FRET pair. The ability to choose fluorophores based on their individual spectral properties beyond the requirements of FRET as well as the versatility of tuning FRET efficiency would open new avenues in engineering FRET-based reporters as well as reporters based on other signaling moieties.

In one embodiment, the invention provides a FRET circuit containing three fluorophores, in which the donor transfers energy to an intermediate fluorophore which then transfers energy to the acceptor. In this manner, the donor and acceptor do not need to meet the requirements of FRET, as the intermediate fluorophore or tuner efficiently couples the two. For example, cyan fluorescent protein (CFP) and red fluorescent protein (RFP) do not meet the requirements of a good FRET pair as very little of the CFP emission spectrum overlaps the excitation spectrum of RFP. However, yellow fluorescent protein (YFP) can serve as a FRET acceptor for CFP and donor for RFP. Thus, a functional FRET circuit can be made from these three fluorophores. By flanking a molecular switch with three fluorophores, as described below, a reporter can be generated with a ratiometric readout of substantial range. See Example 1, which describes use of a circuit of cyan, yellow and red fluorescent proteins with a protein kinase A reporter to provide a reporter with different spectral properties and increased dynamic range.

The ability to choose fluorophores with varying spectral properties in constructing FRET-circuit-based reporters allows simultaneous use of fluorescent compounds that cannot be used otherwise. This is particularly useful as these fluorescent reporters find widespread uses in cellular mechanistic studies or in high-throughput compound screening, where fluorescent compound interference is an important issue. "Tuning" the ratio of sequential versus direct energy transfer may be used to change the properties of a reporter, for example to maximize the change in FRET. Strategies for tuning such reporters with any given FRET donor and acceptor include choosing tuners with different spectral properties and linker engineering, altering FRET efficiencies.

There are multiple triplets that can constitute a tunable FRET or bioluminescent resonance energy transfer (BRET) system using the basic parameters described above. In Example 1, mCFP is the donor, mYFP is the tuner, and mRFP is the acceptor of a tunable FRET system. However, any or all of these fluorescent proteins can be replaced with a fluorescent dye. For example, mCFP can be placed with the biarsenical dyes FlAsH and ReAsH as tuner and acceptor, respectively. In a purely organic system, all fluorescent proteins could be replaced by their spectral equivalents in the Alexa Fluor family of fluorescent compounds. This would call for Alexa Fluor-488 to replace mCFP, Alexa Fluor-555 to replace mYFP, and Alexa Fluor-633 to replace mRFP. This tunable FRET system would be advantageous for in vitro settings. Also advantageous within in vitro settings is the use of a quantum dot as the donor molecule of choice. As an example, Qdot-525 can act as donor to the tuner orange fluorescent protein (OFP) which then donates energy to ReAsH or other red-shifted organic dyes.

Tunable RET also is useful for in vivo imaging, in which the use of bioluminescent proteins and red-shifted fluorophores is helpful for transmission of signal through tissue. In this case, the donor within the system could be a bioluminescent protein creating a tunable BRET system. *Renilla* luciferase paired with coelenterazine-h as substrate could act as a BRET donor to mYFP which could then donate energy to mRFP via FRET. A variation of this system would be tunable $BRET^2$ in which *Renilla* luciferase was paired with Deep Blue-C as substrate, allowing mGFP to act as tuner and mOFP or mRFP as acceptor. As another example, for a far red-shifted readout, firefly luciferase can be a donor, passing energy to mRFP, the tuner, which then donates energy to Alexa Fluor 680. This embodiment is particularly useful for showing clearly detectable signals in in vivo imaging setups.

Tunable RET permits efficiencies between each pair in a RET circuit to be adjusted (for example, CFP to YFP or YFP to RFP) to optimize reporter performance. In addition, tunable FRET can assist in avoiding various sources of interfering fluorescence such as cell autofluorescence or inherent drug fluorescence by allowing the researcher to choose FRET partners with spectral properties that avoid these problems.

This tunable RET system can be readily applied to any reporter based on RET to optimize its performance for a desired application. Such reporters include, but are not limited to, kinase reporters (e.g., those disclosed in WO2007/050734), cAMP reporters (e.g., those disclosed in US 2007/0111270), and the MAPK and phosphatase reporters described below. Of course, tuning of each probe will involve linker length adjustments, changing of the intermediate fluorophore or tuner, and changing the RET donor and acceptor to achieve desired fluorescence properties with high signal amplitude. These adjustments are routine and are well within the skill of the art.

Bimolecular Indicator Reporters

Bimolecular indicator reporters (BindR) take advantage of both RET technology and the latest approaches in protein complementation as readout of enzyme activity. BindR also can be constructed using other forms of readout (e.g., complementation of fluorescent proteins, beta lactamase, *Gaussia* luciferase, TEV protease).

Bimolecular indicator reporters of the invention can be used to monitor activity of a wide range of target enzymes, particularly kinases. Whereas previous reporters have taken advantage of kinase-induced protein-protein interactions between native cell proteins, this approach is limited in that it cannot be generalized to many kinases because the phosphorylation sites on native proteins are preset and may or may not be malleable. In contrast, kinase-induced bimolecular indicator reporters of the invention can be adjusted to accommodate multiple kinase specificities. This type of reporter also facilitates the use of protein complementation as a readout for kinase activity.

One embodiment of a bimolecular indicator reporter is a simple, kinase-inducible switch containing two polypeptides: a phosphoamino acid binding domain (PAABD) and a kinase substrate. Upon phosphorylation of the substrate by the kinase of interest, the PAABD will bind it, which is the basis of this kinase-dependent protein-protein interaction. Example 2 describes a BindR comprising a forkhead associated domain 1 (FHA1) of the yeast protein rad53p as the PAABD. FHA1 is a useful PAABD because it has very few requirements for binding other than a phosphothreonine followed by an aspartate in the +3 position of its ligand. Other PAABDs include, but are not limited to, an FHA2 phosphothreonine binding domain from rad53p, 14-3-3, WW domain, SH2 domains, and the like.

Kinase substrates include, but are not limited to, phosphorylatable domains such as LRRATLVDGGTGGS (SEQ ID NO:18), RFRRFQTLKDKAKAGGTGGS (SEQ ID NO:19), RFRRFQTLKIKAKA (SEQ ID NO:20), KKKKKRFSFKKSFKLSGFSFKKNLL (SEQ ID NO:21), KRFSSKKSFKLSGFSFKKKNKKEA (SEQ ID NO:22), KRFSSKKSFKLSGFSFKKKSKKEA (SEQ ID NO:23), KKFSSKKPFKLSGFSFR (SEQ ID NO:24), ETTSSFKKFFTHGTGFKKSKEDD (SEQ ID NO:25), KLFSSSGLKKLSGKKQKGKRGGG (SEQ ID NO:26), EGITPWASFKKMVTPKKRVRRPS (SEQ ID NO:27), and EGVSTWESFKRLVTPRKKSKSKL (SEQ ID NO:28).

Improved Akt Activity Reporters

The invention also provides improved, specific, and reversible Akt activity reporters termed AktARs. AktARs of the invention can report endogenous Akt activity with a ~40% increase in emission ratios of yellow over cyan, which is five times that of BKAR (Kunkel, 2005). Because of its robust signal, AktAR is able to detect subtle changes in subcellular Akt activity, providing a much-needed tool for investigating the Akt activity dynamics within subcellular membrane compartments.

The AktAR reporter is based on Akt activity dependent changes in FRET between CFP and YFP. Akt phosphorylates the substrate region of the reporter, increasing the ratio of cyan to yellow emissions by ~40%, which can be reversed by inhibition of the PI3K activity. The reporter can be targeted to different subcellular locations (e.g., plasma membrane, nucleus, and mitochondria). Targeted versions of AktAR reporters can provide valuable information towards understanding of Akt activation in living cells.

MAPK Reporters

This invention describes emission ratiometric reporters for measuring intracellular mitogen activated protein kinases (MAPK) activity in living tissues and cells, in particular c-Jun N-terminal kinase (JNK) and extracellular-signal-regulated kinase (ERK), with high spatial and temporal resolution and in high throughput assays. These chimeric protein reporters are encoded by nucleic acid constructs that can be transferred into a living cell, allowing expression of the protein reporter within the cell. The reporters are based on phosphorylation dependent changes in RET, for example, between two color variants of Green Fluorescence Protein (GFP). In some embodiments, JNK activity increases the ratio of yellow to cyan emissions by 10-35%. These genetically encoded reporters and various fusions for targeting to cellular locations (e.g., plasma membrane, nucleus, and mitochondria) provide tools for the flexible, reliable and quantifiable measurements of JNK activity. In another embodiment, reporters detect changes in ERK activity.

The MAPK reporters of the invention comprise (a) a donor moiety; (b) a PAABD (e.g., an FHA1 polypeptide) linked to the donor moiety; (c) a substrate peptide for the MAPK enzyme linked to the PAABD; and (d) an acceptor moiety linked to the polypeptide. Upon phosphorylation of the substrate peptide, an interaction between FHA1 and the phosphorylated substrate results in a conformation change in the reporter protein that brings the donor and acceptor moieties into close proximity and alters the resonance energy transfer between the moieties. The degree of alteration reflects MAPK activity levels and can be detected qualitatively or quantitatively.

MAPK reporters of the invention have some unique advantages over previous methods for assessing MAPK dynamics inside cells. They do not require destroying large amounts of cells or tissue, and provides high spatial and temporal resolution. They also can be targeted to different subcellular sites or fused to signaling components and has the flexibility of measuring changes in MAPK activity within various subcellular compartments.

Other versions of fluorescent proteins can be used, and reporters can be constructed to detect the specific isoforms of JNK (e.g. JNK1, JNK2, JNK3). These reporters can be targeted to additional subcellular sites and fused to other signaling components.

In the preferred embodiment of the JNK reporter, the transcription factor JDP2 is the substrate peptide because it has been shown to be efficiently phosphorylated by JNK. It also contains a docking site for JNK that lies immediately c-terminal to the phosphoacceptor domain. This may be important in order to allow access of the phosphorylated substrate to FHA1. The +3 position relative to the phosphoacceptor was mutated to aspartate to facilitate FHA1 binding. FHAI can bind to phosphothreonine containing proteins and prefers an aspartate at the +3 position. The GFP variants ECFP and citrine can be used as the donor and acceptor moieties, respectively, and function as FRET pairs to measure the resonance energy transfer. Upon phosphorylation of the JDP2 domain, interaction between FHA1 and the substrate will bring the two GFP variants into close proximity so that an increase in FRET correlates with phosphorylation.

Phosphatase Activity Reporters

Figure 19:
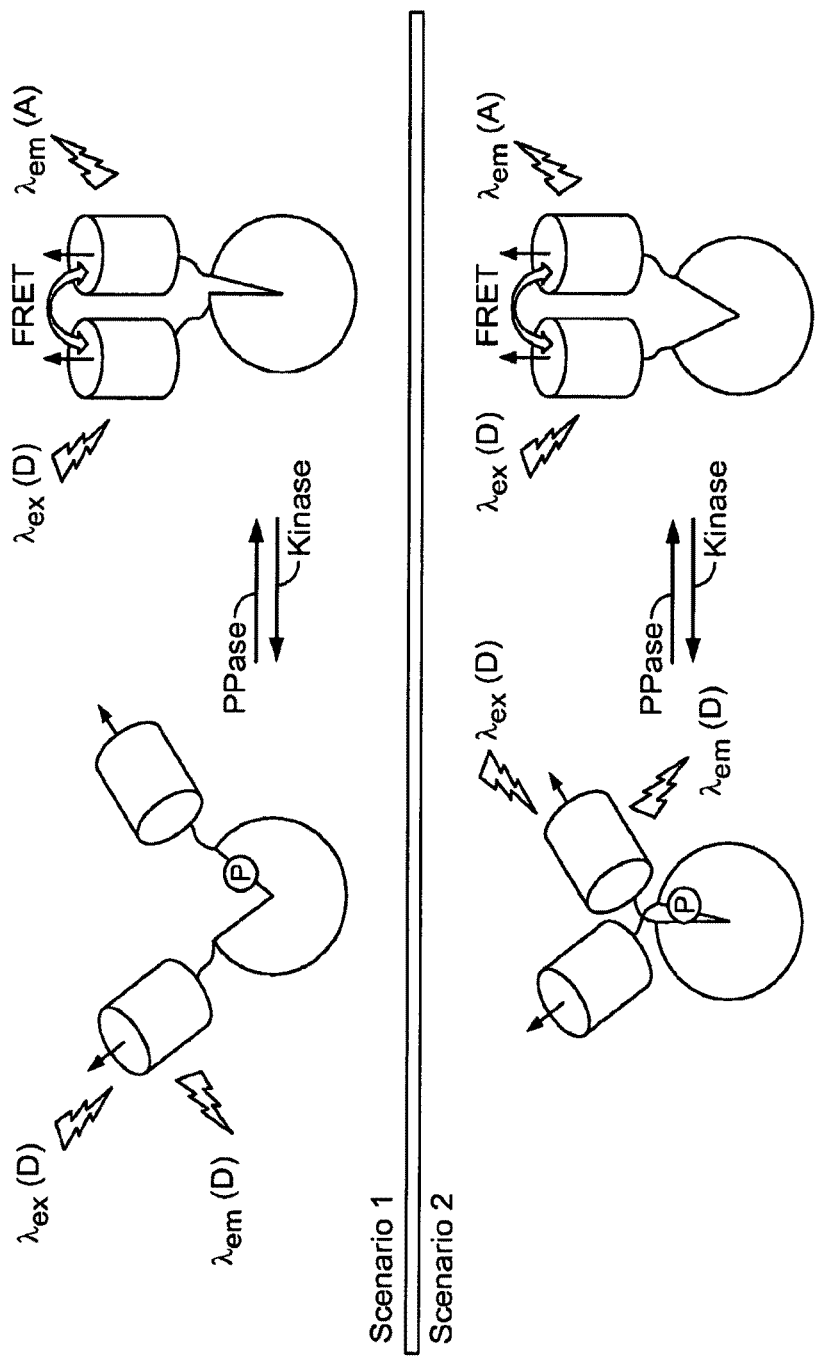
FIG. 19. General design of a FRET-based phosphatase activity reporter. Two possible scenarios, each leading to increased FRET, are shown. The basic reporter design contains a phosphatase activity-dependent molecular switch (light gray) sandwiched between a FRET donor (D; dark gray cylinder) and a FRET acceptor (A; light gray cylinder). Dephosphorylation-dependent conformational changes in the substrate region cause a change in interfluorophore distance and/or reorientation of the fluorophore dipoles ($\updownarrow$) resulting in an increase in FRET (curved arrow). PPase, protein phosphatase; $\lambda_{ex}(D)$, excitation wavelength of the donor fluorophore; $\lambda_{em}(D)$, emission wavelength of the donor fluorophore; $\lambda_{em}(A)$, emission wavelength of the acceptor fluorophore.

The invention provides genetically-encoded RET-based phosphatase activity reporters, based on a generalizable design, which use a molecular switch that is sensitive to the activity of a phosphatase of interest (FIG. 19). One embodiment of this reporter ("CaNAR1") was designed to track the activity of the serine/threonine protein phosphatase, calcineurin, within its endogenous environment and is described in Example 5. CaNAR reports endogenous calcineurin activity with a 5-15% increase in emission ratios of yellow over cyan. The CaNAR uses an intrinsic conformational change within the regulatory region of NFAT1 to re-orient CFP and YFP in space and is phosphorylated in resting cells due to the activity of intracellular protein kinases such as casein kinase-1α and p38. Increased intracellular calcium activates calcineurin, thereby promoting dephosphorylation of the substrate region of the reporter. Dephosphorylation drives a conformational change in the reporter, leading to a 5-15% increase in the ratio of cyan to yellow emissions. The observed response, which is fully reversible, can be abolished by inhibition of calcineurin activity by the calcineurin-specific inhibitor, cyclosporine A. This reporter can be used to provide valuable information about the regulation of calcineurin activation inside living cells. Using this indicator, calcineurin activity can be monitored in living cells in real time. It can also be targeted to different subcellular sites or fused to signaling components and has the flexibility of measuring calcineurin activity changes within various subcellular compartments. The reporter can also be used as a high throughput assay for drug screening and diagnostic analysis.

For example, CaNAR1 can be used to track calcineurin activity in Jurkat T cells, cardiomyocytes and several neuronal cell lines (e.g., GT17 and PC12) to better understand the role of calcineurin in T cell activation, cardiac hypertrophy and long term potentiation, respectively. The reporter will also be targeted to various subcellular compartments (e.g., ER, plasma membrane, nucleus) to examine the contribution select pools of calcineurin in these and other cellular processes.

The phosphatase activity reporter design illustrated here is generally applicable to other protein phosphatases for which specific molecular switches can be engineered. For example, CaNAR1 can be converted from a calcineurin-specific reporter into a PP2A-specific reporter by exchanging the endogenous calcineurin docking site of NFAT1 with a PP2A docking site. A similar approach may also be taken for other protein phosphatases, such as protein phosphatase 1 (PP1).

Methods of Making and Using Reporters of the Invention

Reporters described above can be constructed using components and methods described below and in the specific examples.

Donor and Acceptor Moieties

As used here, a "donor moiety" is a fluorophore or a luminescent moiety. The absorption spectrum of the "acceptor moiety" overlaps the emission spectrum of the donor moiety. The acceptor moiety does not need to be fluorescent and can be a fluorophore, chromophore, or quencher. In some embodiments both the donor and acceptor moieties are fluorescent proteins. In other embodiments both the donor and acceptor moieties are luminescent moieties. In yet other embodiments, either one of the donor or acceptor moieties can be a fluorescent protein while the other moiety is a luminescent moiety. In other embodiments, the acceptor moiety is a "quencher moiety."

When both the donor and acceptor moieties are fluorophores, resonance energy transfer is detected as fluorescence resonance energy transfer (FRET). If a luminescent moiety is involved, resonance energy transfer is detected as luminescent resonance energy transfer (LRET). LRET includes bioluminescent resonance energy transfer (BRET; Boute et al., *Trends Pharmacol. Sci.* 23, 351-54, 2002; Ayoub et al., *J. Biol. Chem.* 277, 21522-28, 2002). Because excitation of the donor moiety does not require exogenous illumination in an LRET method, such methods are particularly useful in live tissue and animal imaging, because penetration of the excitation light is no longer a concern. LRET methods have a high contrast and high signal-to-noise ratio; 2) no photobleaching occurs; and 3) quantification is simplified because the acceptor moiety is not directly excited.

Suitable acceptor moieties include, for example, a coumarin, a xanthene, a fluorescein, a fluorescent protein, a circularly permuted fluorescent protein, a rhodol, a rhodamine, a resorufin, a cyanine, a difluoroboradiazaindacene, a phthalocyanine, an indigo, a benzoquinone, an anthraquinone, an azo compound, a nitro compound, an indoaniline, a diphenylmethane, a triphenylmethane, and a zwitterionic azopyridinium compound.

Suitable donor moieties include, but are not limited to, a coumarin, a xanthene, a rhodol, a rhodamine, a resorufin, a cyanine dye, a bimane, an acridine, an isoindole, a dansyl dye, an aminophthalic hydrazide, an aminophthalimide, an aminonaphthalimide, an aminobenzofuran, an aminoquinoline, a dicyanohydroquinone, a semiconductor fluorescent nanocrystal, a fluorescent protein, a circularly permuted fluorescent protein, and fluorescent lanthanide chelate.

Fluorescent Proteins

In some preferred embodiments either or both of the donor and acceptor moieties is a fluorescent protein. Suitable fluorescent proteins include green fluorescent proteins (GFP), red fluorescent proteins (RFP), yellow fluorescent proteins (YFP), and cyan fluorescent proteins (CFP). Useful fluorescent proteins also include mutants and spectral variants of these proteins which retain the ability to fluoresce.

RFPs include Discosoma RFPs, such Discosoma DsRed or a mutant thereof which includes an Ile125Arg mutation, or a non-oligomerizing tandem DsRed containing, for example, two RFP monomers linked by a peptide linker. For example, a non-oligomerizing tandem RFP can contain two DsRed monomers or two mutant DsRed-I125R monomers linked by a peptide.

Useful GFPs include an *Aequorea* GFP, a *Renilla* GFP, a *Phialidium* GFP, and related fluorescent proteins for example, a cyan fluorescent protein (CFP), a yellow fluorescent protein (YFP), or a spectral variant of the CFP or YFP. CFP (cyan) and YFP (yellow) are color variants of GFP. CFP and YFP contain 6 and 4 mutations, respectively. They are Tyr66Try, Phe66Leu, Ser65Thr, Asn145Ile, Met153Thr, and Val163Ala in CFP and Ser65Gly, Val168Leu, Ser72Ala, and Thr203Tyr. Spectral variants include an enhanced GFP (EGFP), an enhanced CFP (ECFP), an enhanced YFP (EYFP), and an EYFP with V68L and Q69K mutations. Other examples of fluorescent proteins comprising mutations are *Aequorea* GFP with one or more mutations at amino acid residues A206, L221 or F223 (e.g., mutations A206K, L221K, F223R, Q80R); mutations L221K and F223R of ECFP, and EYFP-V68L/Q69K. See also US 2004/0180378; U.S. Pat. Nos. 6,150,176; 6,124,128; 6,077,707; 6,066,476; 5,998,204; and 5,777,079; Chalfie et al., Science 263:802-805, 1994.

Other useful GFP-related fluorescent proteins include those having one or more folding mutations, and fragments of the proteins that are fluorescent, for example, an *A. victoria* GFP from which the two N-terminal amino acid residues have been removed. Several of these fluorescent proteins contain different aromatic amino acids within the central chromophore and fluoresce at a distinctly shorter wavelength than the wild type GFP species. For example, the engineered GFP proteins designated P4 and P4-3 contain, in addition to other mutations, the substitution Y66H; and the engineered GFP proteins designated W2 and W7 contain, in addition to other mutations, Y66W.

Folding mutations in *Aequorea* GFP-related fluorescent proteins improve the ability of the fluorescent proteins to fold at higher temperatures and to be more fluorescent when expressed in mammalian cells, but have little or no effect on the peak wavelengths of excitation and emission. If desired, these mutations can be combined with additional mutations that influence the spectral properties of GFP to produce proteins with altered spectral and folding properties, and, particularly, with mutations that reduce or eliminate the propensity of the fluorescent proteins to oligomerize. Folding mutations, with respect to SEQ ID NO:11, include the substitutions F64L, V68L, S72A, T44A, F99S, Y145F, N146I, M153T, M153A, V163A, I167T, S175G, S205T, and N212K.

Luminescent Moieties

Luminescent moieties useful in reporters of the invention include lanthanides, which can be in the form of a chelate, including a lanthanide complex containing the chelate (e.g., β-diketone chelates of cerium, praseodymium, neodymium, promethium, samarium, europium, gadolinium, terbium, dysprosium, holmium, erbium, thulium, or ytterbium). Lanthanide chelates are well known in the art. See Soini and Kojola, Clin. Chem. 29, 65, 1983; Hemmila et al., Anal. Biochem. 137, 335 1984; Lovgren et al., In: Collins & Hoh, eds., Alternative Immunoassays, Wiley, Chichester, U.K., p. 203, 1985; Hemmila, Scand. J. Clin. Lab. Invest. 48, 389, 1988; Mikola et al., Bioconjugate Chem. 6, 235, 1995; Peruski et al., J. Immumol. Methods 263, 35-41, 2002; U.S. Pat. No. 4,374,120; and U.S. Pat. No. 6,037,185. Suitable β-diketones are, for example, 2-naphthoyltrifluoroacetone (2-NTA), 1-naphthoyltrifluoroacetone (1-NTA), p-methoxybenzoyltrifluoroacetone (MO-BTA), p-fluorobenzoyltrifluoroacetone (F-BTA), benzoyltrifluoroacetone (BTA), furoyltrifluoroacetone (FTA), naphthoylfuroylmethane (NFM), dithenoylmethane (DTM), and dibenzoylmethane (DBM). See also US 20040146895.

Luminescent proteins include, but are not limited to, lux proteins (e.g., luxCDABE from *Vibrio fischerii*), luciferase proteins (e.g., firefly luciferase, *Gaussia* luciferase, *Pleuromamma* luciferase, and luciferase proteins of other beetles, Dinoflagellates (*Gonyaulax; Pyrocystis*;), Annelids (*Dipocardia*), Molluscs (*Lativa*), and Crustacea (*Vargula; Cypridina*), and green fluorescent proteins of bioluminescent coelenterates (e.g., *Aequorea Victoria, Renilla mullerei, Renilla reniformis*; see Prendergast et al., Biochemistry 17, 3448-53, 1978; Ward et al., Photochem. Photobiol. 27, 389-96, 1978; Ward et al., *J. Biol. Chem.* 254, 781-88, 1979; Ward et al., Photochem. Photobiol. Rev 4, 1-57, 1979; Ward et al., Biochemistry 21, 4535-40, 1982). Many of these proteins are commercially available. Firefly luciferase is available from Sigma, St. Louis, Mo., and Boehringer Mannheim Biochemicals, Indianapolis, Ind. Recombinantly produced firefly luciferase is available from Promega Corporation, Madison, Wis. Jellyfish aequorin and luciferase from *Renilla* are commercially available from Sealite Sciences, Bogart, Ga.

The DNA sequences of the aequorin and other luciferases employed for preparation of some MAPK reporters of the invention can be derived from a variety of sources. For example, cDNA can be prepared from mRNA isolated from the species disclosed above. See Faust, et al., *Biochem.* 18, 1106-19, 1979; De Wet et al., *Proc. Natl. Acad. Sci. USA* 82, 7870-73, 1985.

Luciferase substrates (luciferins) are well known and include coelenterazine (available from Molecular Probes, Eugene, Oreg.) and ENDUREN™. These cell-permeable reagents can be directly administered to cells, as is known in the art. Luciferin compounds can be prepared according to the Methods disclosed by Hori et al., *Biochemistry* 14, 2371-76, 1975; Hori et al., *Proc. Natl. Acad. Sci. USA* 74, 4285-87, 1977).

Dark Quenchers

In some embodiments the acceptor moiety is a quencher moiety, preferably a "dark quencher" (or "black hole quencher") as is known in the art. "Dark quenchers" themselves do not emit photons. Use of a "dark quencher" reduces or eliminates background fluorescence or luminescence which would otherwise occur as a result of energy transfer from the donor moiety. Suitable quencher moieties include dabcyl (4-(4'-dimethylaminophenylazo)-benzoic acid), QSY™-7 carboxylic acid, succinimidyl ester (N,N'-dimethyl-N,N'-diphenyl-4-((5-t-butoxycarbonylaminopentyl) aminocarbonyl) piperidinylsulfone-rhodamine (a diarylrhodamine derivative from Molecular Probes, Eugene, Oreg.). Suitable quencher moieties are disclosed, for example, in US 2005/0118619; US 20050112673; and US 20040146959.

Any suitable fluorophore may be used as the donor moiety provided its spectral properties are favorable for use with the chosen dark quencher. The donor moiety can be, for example, a Cy-dye, Texas Red, a Bodipy dye, or an Alexa dye. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, a fluorescein (e.g., fluorescein, tetrachlorofluorescein, hexachlorofluorescein), rhodamine, tetramethylrhodamine, or other like compound. Suitable fluorescent moieties for use with dark quenchers include xanthene dyes, such as fluorescein or rhodamine dyes, including 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N;N'-tetramethyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS).

Other suitable fluorescent moieties include coumarins, such as 3-phenyl-7-isocyanatocoumarin; acridines, such as 9-isothiocyanatoacridin-e and acridine orange; N-(p-(2-benzoxazolyl)phenyl)maleimide; cyanines, such as indodicarbocyanine 3 (Cy3), indodicarbocyanine 5 (Cy5), indodicarbocyanine 5.5 (Cy5.5), 3-1-carboxy-pentyl)-3'-ethyl-5,5'-dimethyl-loxacarbocyanine (CyA); 1H,5H,1H,15H-Xantheno[2,3,4-ij:5,6,7-i'j']diquinol-izin-18-ium, 9-[2(or 4)-[[[6-[2,5-dioxo-1-pyrrolidinyl)oxy]-6-oxohexyl]amino] isulfonyl]-4(or 2)-sulfophenyl]-2,3,6,7,12,13,16,17-octahyd-ro-inner salt (TR or Texas Red); BODIPY™ dyes; benzoxaazoles; stilbenes; pyrenes; and the like.

Delivery of Reporters to Cells

Reporters of the invention can be introduced into cells in vitro using reversible permeabilization techniques. See U.S.

Pat. No. 6,127,177; U.S. Pat. No. 6,902,931; Russo et al., *Nature Biotechnology* 15, 278-82, March 1997; Santangelo et al., *Nucleic Acids Res.* 32, 1-9, Apr. 14, 2004.

If a reporter is a fusion protein, expression vectors comprising a reporter-encoding nucleotide sequence can be transfected into any cell in vitro in which it is desired to monitor enzyme levels or distribution. Any transfection method known in the art can be used, including, for example, including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Useful vectors and methods of delivering the vectors to cells in vivo are disclosed, for example, in U.S. Pat. No. 6,825,012; U.S. Pat. No. 6,878,549; U.S. Pat. No. 6,645,942; U.S. Pat. No. 6,692,737; U.S. Pat. No. 6,689,758; U.S. Pat. No. 6,669,935; and U.S. Pat. No. 6,821,957.

Subcellular Targeting

Subcellular targeting sequence which can target a reporter of the invention to a subcellular domain, such as a plasma membrane, a nuclear membrane, a cytosol, an endoplasmic reticulum, a mitochondria, a mitochondrial matrix, a chloroplast, a medial trans-Golgi cisternae, a lumen of a lysosome, or a lumen of an endosome, are well known in the art. Examples include the plasma membrane targeting sequence shown in SEQ ID NO:2, the nuclear localization signal sequence shown in SEQ ID NO:1, the mitochondrial localization sequence shown in SEQ ID NO:3, and the mitochondrial matrix targeting signal shown in SEQ ID NO:4. Targeting sequences can be linked to a reporter using, for example, a tetracysteine motif such as Cys Cys Xaa Xaa Cys Cys (SEQ ID NO:5). Targeting sequences can be linked at either the N- or C-terminus of a reporter or at intermediate points in the reporter.

Methods of Detecting Enzymatic Activity

The invention provides various methods for detecting enzymatic activity by detecting conformational changes in a reporter of the invention. Broadly, the methods involve detecting a change in resonance energy transfer of a reporter of the invention when the reporter is subjected to an increase or decrease in enzymatic activity. The enzyme acts on the substrate portion of the relevant reporter to induce a conformational change that changes resonance energy transfer from the donor moiety to the acceptor moiety.

A change in resonance energy transfer can readily be detected using methods well known in the art. See, e.g., US 2005/0118619; US 2002/0137115; US 2003/0165920; US 2003/0186229; US 2004/0137479; US 2005/0026234; US 2005/0054573; US 2005/0118619; U.S. Pat. No. 6,773,885; U.S. Pat. No. 6,803,201; U.S. Pat. No. 6,818,420; Ayoub et al., 2002; Boute et al., 2002; Domin et al., *Prog. Biomed. Optics and Imaging, Proc. SPIE*, vol 5139, 2003, pp 238-242; Evellin et al., *Methods Mol. Biol.* 284, 259-70, 2004; Honda et al., *Proc. Natl. Acad. Sci. USA* 98, 437-42, Feb. 27, 2001; Honda et al., *Methods Mol. Biol.* 3, 27-44, 1005; Mongillo et al., *Cir. Res.* 95, 67-75, Jul. 9, 2004; Mongillo et al., *Methods Mol. Biol.* 307, 1-14, 2005; Nagai et al., *Proc. Natl. Acad. Sci. USA* 101, 10554-59, Jul. 20, 2004; Nikolaev et al., *J. Biol. Chem.* 279, 37215-18, 2004; Polit et al., *Eur. J. Biochem.* 270, 1413-23, 2003; Ponsioen et al., *EMBO Rep.* 5, 1176-80, 2004; Santangelo et al., *Nucl. Acids Res.* 32, 1-9, e-published Apr. 14, 2004; and Warrier et al., *Am. J. Physiol. Cell Physiol.* 289, C455-61, August 2005. Properties which can be detected as resonance energy transfer (RET) measurements include a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, anisotropy, a polarization of emitted light, resonance energy transfer, and a quenching of emission at a wavelength.

Reporters of the invention can be used in cell-free systems, in isolated cells (for example, in primary cell culture or a cell line) or in cells in situ (e.g., in an isolated tissue sample, an isolated whole organ, or in a mammal). Absolute activity levels can be detected by obtaining a RET measurement in the assay system and comparing it to a standard curve obtained in vitro.

In some embodiments, steady-state RET measurements are first obtained and then measurements are taken after addition of a test compound to the assay system. The effects of the test compounds on enzymatic activity can be monitored by using a reporter (e.g., in drug-screening methods). Test compounds can be pharmacologic agents already known in the art to affect enzyme activity or can be compounds previously unknown to have such an activity.

Test compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection.

Fluorescence activated cell sorting (FACS) is well-suited for use with high throughput methods of the invention. For example, emission ratios of yellow-to-cyan (cyan excitation) for individual cells are detected during the first sorting—not all cells will have the same emission ratio and a distribution for the whole population can be plotted; the cells can be stimulated to activate an enzyme in the absence or presence of other drugs; emission ratios of individual cells are detected again during the second sorting; the difference in emission ratios, usually presented as a shift in the distribution, will reflect the changes in enzymatic activity.

High-Throughput Assays

High throughput assays of the invention are generally applicable to all kinase targets within the kinome and are ideally suited for examining dynamic responses of endogenous kinase targets, for evaluating drug candidates which ultimately perform within cellular environments, and for identifying compounds with unique mechanisms of action. Methods of the invention can be extended to follow multiple components of kinase-mediated signaling pathways to screen for pathway modulators.

High throughput assays of the invention, when combined with use of activity reporters, permit simple, fast, and convenient high-throughput reading of dynamic kinase activities with high spatiotemporal resolution. These methods complement, yet offer unique advantages over, existing methods, including purified target-based biochemical screens and endpoint focused phenotypic screens. Activity-based screens of the invention can be combined with phenotypic screens (e.g., Clemons, Curr. Op. Chem. Biol. 8, 334-38, 2004) to provide direct measurement of dynamic cellular activities of defined targets or the activity of a signaling pathway. Compared to in vitro assays, living cells are used as reaction vessels with targets of interest, cofactors, and regulators present at endogenous levels in their natural cellular environment, where spatiotemporal control of signaling activities can be specifically followed. With the complexity of live systems maintained, the quality of the screening process is increased, enabling discovery of compounds with unique mechanisms of action. Thus, the simple yet powerful high-throughput activity assays of the invention should find immediate application in high-throughput screens for pharmacological reagents and drug candidates, as well as in parallel tracking of multiple physiological and pharmacological events at subcellular locations in living cells in chemical and functional genomics studies. Furthermore, this assay platform is generally applicable to most kinases in the kinome, as various kinase activity reporters can be engineered and adapted to this assay format.

Kits

The invention provides kits comprising one or more reporters of the invention. The kits also may provide all or a subset of the reagents that are required for practicing the invention. The kits may comprise written instructions, in paper or electronic form, or a reference to an on-line set of instructions. The instructions may contain data against which the results determined using the kit can be compared. Containers which hold the components of any given kit can vary. The kits may be divided into compartments or contain separate vessels for each component. The components may be mixed together or may be separated. Optional components of the kit include means for collecting, processing, and/or storing test samples.

All patents, patent applications, and references cited in this disclosure are expressly incorporated herein by reference in their entirety. The above disclosure generally describes the present invention. A more complete understanding can be obtained by reference to the incorporated specific examples, which are provided for purposes of illustration only and are not intended to limit the scope of the invention.

Example 1

Tunable FRET

Gene Construction

The gene encoding Cerulean was PCR amplified using primers that introduce a 5'-BamHI and 3'-SphI site in the case of CRY AKAR and a 5'-SacI and 3'-EcoRI site in the case of RYC AKAR. The gene for Venus (1-227) was PCR amplified using a primer that introduces a 5'-KpnI site for both CRY AKAR and RYC AKAR paired with reverse primers that introduce 3'-EcoRI and 3'-SphI sites in CRY AKAR and RYC AKAR respectively. The gene for mCherry was PCR amplified using primers that introduce a 5'-SacI site and 3'-KpnI site for insertion into CRY AKAR and 5'-BamHI and 3'-KpnI sites in the case of RYC. CR AKAR required introduction of a 5'-SacI and 3'-EcoRI site to mCherry via PCR. PCR products then underwent restriction digestion followed by ligation into the appropriate sites in AKAR3. Complete genes for CRY AKAR and RYC AKAR were then subcloned into pCDNA3' behind a Kozak sequence for mammalian expression.

Cell Culture and Imaging

HEK-293 or HeLa cells were plated onto sterilized glass coverslips in 35 mm dishes and grown to ~50% confluency in DMEM (10% FBS (m/v) at 37° C. with 5% $CO_2$). Cells underwent Fugene 6-mediated transfection and allowed to grow for 12-24 hours before imaging. After washing once with Hanks' balanced salt solution (HBSS), cells were maintained in buffer in the dark at 20-25° C., and treated with various reagents as indicated. Cells were imaged on a Zeiss Axiovert 200M microscope with a 40×11.3NA oil-immersion objective lens and cooled CCD camera. Dual emission ratio imaging used a 420DF20 excitation filter, a 600DRLP dichroic mirror, and two emission filters (475DF40 for cyan and 653DF95 for red). The ratios of red-to-cyan were then calculated at different time points and normalized by dividing all ratios by the emission ratio before stimulation, setting basal emission ratio as 1. mCherry photobleaching utilized a 565DF55 excitation filter with 600DRLP dichroic mirror; cells were illuminated in this way for 25 minutes. Venus photobleaching utilized a 525DF40 excitation filter with 600DRLP dichroic mirror. Cells were illuminated for 5 minutes.

Calculation of FRET Efficiencies

FRET efficiencies between each FRET pair were calculated based on donor recovery after acceptor photobleaching. EDA represents FRET efficiency between donor (D) and acceptor (A). Efficiencies were calculated using the following equation in which ID and IDA represent the measured intensity of the donor fluorophore in the absence and presence of acceptor respectively.

$$E_{DA} = 1 - \frac{I_{DA}}{I_D}$$

Because CRY AKAR is a three fluorophore system, the FRET efficiencies between Cerulean and mCherry, and Cerulean and Venus were corrected to reflect the true efficiencies when all three fluorophores are present. The correct efficiencies (E'DA) were calculated using the following equations (Galperin et al., *Nat. Methods* 1, 209-17, 2004):

$$E'_{CR} = \frac{E_{CR} - E_{CR}E_{CY}}{1 - E_{CR}E_{CY}}$$

$$E'_{CY} = \frac{E_{CY} - E_{CR}E_{CY}}{1 - E_{CR}E_{CY}}$$

The following three FRET efficiencies: E'CY, E'CR, and EYR were then used to calculate the total efficiency of energy transferred from Cerulean (ETOT) to mCherry via both direct (E'CR) and sequential paths.

$$E_{TOT} = E'_{CY}E_{YR} + E'_{CR}$$

Finally, the percentage of energy traveling from Cerulean to mCherry directly was determined by dividing E'CR by ETOT and multiplying by 100. Logically, the percentage of energy traveling from Cerulean to mCherry along the sequential path would be 100 minus the percentage of energy moving directly to mCherry.

Cyan fluorescent protein (CFP) and red fluorescent protein (RFP), particularly mCherry, have separate emissions but limited spectral overlap and are considered a poor FRET pair. To test our FRET circuit for constructing fluorescent reporters, we built a new A-kinase activity reporter (AKAR) with cyan-red ratiometric readout. A-Kinase Activity Reporter (AKAR) (Zhang et al., *Proc. Natl. Acad. Sci. USA* 98, 14997-15002, 2001; Zhang et al., *Nature* 437, 569-73, 2005; Zhang *Biophys. Biochem. Res. Commun.* 348, 716-21, 2006) measures activity of PKA and usually consists of a FRET pair, a phosphoamino acid binding domain, and a PKA substrate. When phosphorylated by PKA, intramolecular binding of the substrate by the phosphoamino acid binding domain drives conformational reorganization, leading to an increase in FRET. In the new CRY AKAR, a yellow fluorescent protein (YFP) Venus was chosen as a tuner between cyan and red fluorophores based on its appropriate spectral overlap with CFP and RFP. The phosphorylation dependent conformational switch composed of Forkhead associated domain 1 (FHA1) and PKA substrate was sandwiched between Cerulean, a CFP, and mCherry, linked to Venus via a short spacer (FIG. 2A).

To test the presence of a FRET circuit, we calculated FRET efficiencies for the energy transfer processes in CRY AKAR. Energy transfer from Cerulean to mCherry has two potential paths. The first is a direct path from Cerulean to mCherry; the second is sequential energy transfer from Cerulean to Venus then Venus to mCherry. To determine the efficiency of each transfer, HEK 293 cells transiently transfected with either CRY AKAR or a similar construct without Venus were subject to a series of photobleaching procedures. First, cells expressing CRY AKAR underwent RFP photobleaching. At this point, recovery of YFP fluorescence was measured to obtain the FRET efficiency between Venus and mCherry, 36%±2% [average±(stdev.)], (n=5). With mCherry fluorophores irreversibly photobleached, FRET occurs only from Cerulean to Venus. The same cells then underwent YFP photobleaching and CFP recovery was measured to calculate the FRET efficiency between Cerulean and Venus in the absence of mCherry, 19%±3% (n=5). Next, we determined the efficiency of direct energy transfer from Cerulean to mCherry in the absence of Venus by using the two-fluorophore construct. RFP was photobleached and CFP recovery was measured to yield a FRET efficiency of 18%±7% (n=4).

With these three FRET efficiencies, it is straightforward to calculate the percentage of sequential versus direct energy transfer from Cerulean to mCherry. The percentages of sequential and direct energy transfer were found to be approximately 29% and 71%, respectively. Thus, this FRET circuit is functional in CRY AKAR, with Venus acting as an intermediate fluorophore in the sequential energy transfer between Cerulean and mCherry along with a direct energy transfer path. As the efficiency of sequential energy transfer is largely determined by the FRET efficiency between Venus and mCherry, the current 36% leaves room for tuning the efficiency, for example by optimizing the spacer between mCherry and Venus.

Next we tested the cellular responses of CRY AKAR. HeLa cells were transiently transfected, and imaged using appropriate filter sets for cyan and red emissions during cyan excitation. As shown in FIG. 2B, CRY AKAR diffused throughout the cytoplasm and somewhat into the nucleus. Stimulation with the beta-adrenergic receptor agonist isoproterenol (ISO) caused a decrease in cyan emission and an increase in red emission (not shown). Using the ratio of red to cyan emissions as a convenient readout, ISO stimulation yielded an average response of 39%±2% [average±(stdev.)], n=5). After this response reversed following receptor desensitization, cAMP clearance and reporter dephosphorylation, the same cells were treated with the transmembrane adenylyl cyclase activator forskolin (Fsk) yielding a more robust response from CRY AKAR (FIG. 2C). The average response with Fsk stimulation was 54%±6%, n=5, exceeding the dynamic range of AKAR3, currently the best cyan-yellow ratiometric probe in the same series, which has a maximum response of ~40%.

CRY-AKAR successfully tracks intracellular PKA activity with a cyan-red ratiometric readout. Its use in cellular studies should be compatible with the presence of yellow fluorescent compounds, which largely affect reporters based on commonly used CFP-YFP FRET pair. To compare the difference, HeLa cells expressing CRY-AKAR were treated with 50 µM L-sepiapterin, a GTP cyclohydrolase I inhibitor with CFP-like excitation and broad, predominantly yellow emission (FIG. 3A). As shown in FIG. 3B, the presence of L-sepiapterin affected the detection of CFP minimally. However, as expected, the image of yellow fluorescence shows very little contrast between the transfected cell and the background due to the compound fluorescence. On the other hand, the transfected cell was clearly discernable with the detection of red emission upon cyan excitation. Thus, the ability to choose fluorophores with varying spectral properties in constructing FRET-circuit-based reporters allows simultaneous use of fluorescent compounds that cannot be used otherwise. This is particularly useful as these fluorescent reporters find widespread uses in cellular mechanistic studies or in high-throughput compound screening, where fluorescent compound interference is an important issue.

Thus, in a FRET circuit containing Cerulean, Venus, and mCherry, excitation of Cerulean leads to energy transfer to mCherry via both a direct and sequential path. "Tuning" the ratio of sequential versus direct energy transfer may be used to change the properties of the reporter, for example to maximize the change in FRET. Strategies for tuning such reporters with any given FRET donor and acceptor include choosing tuners with different spectral properties and linker engineering, altering FRET efficiencies.

This tunable FRET system has led to the development of an improved AKAR with cyan-red ratiometric readout for more versatile use in live cell analysis. The same FRET is applicable to other FRET-based reporters, such as second messenger indicators (Nagai et al., *Proc. Natl. Acad. Sci. USA* 101, 10554-59, 2004; Palmer et al., *Chem. Biol.* 13, 521-30, 2006; DiPilato et al., *Proc. Natl. Acad. Sci. USA* 101, 16513-18, 2004; Ananthanarayanan et al., *Proc. Natl. Acad. Sci. USA* 102, 15081-86, 2005). As an extension, tunable FRET should allow the use of two spectrally distant fluorophores as FRET donor and acceptor. The only requirement is that there exists a fluorophore that serves as a FRET acceptor for the donor of choice and FRET donor for the acceptor of choice which is spectrally distinguishable from the donor and acceptor. When these criteria are met, fluorophores can be chosen for their unique spectral properties, which could assist in avoiding overlap with cell autofluorescence or drug fluorescence or for high photostability in specific in vitro or live cell environments. The concept of tunable FRET is also applicable to fluorescent dyes, quantum dots, and even bioluminescent proteins for tunable bioluminescence resonance energy transfer (BRET).

Example 2

Bimolecular Indicator Reporters for PKA and PKC

Figure 7:
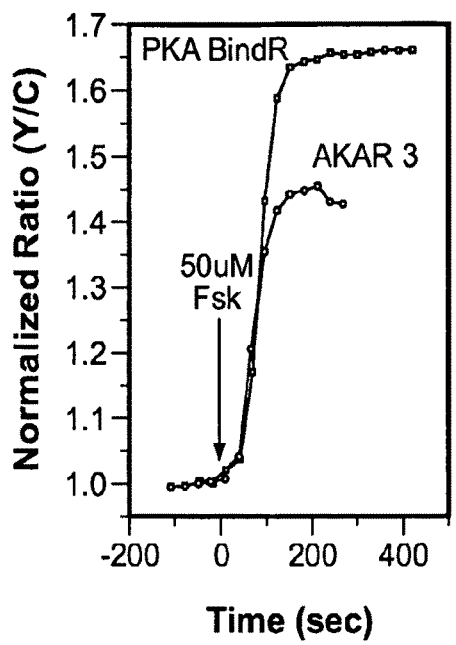
FIG. 7. Emission ratio time courses of a PKA BindR and a unimolecular PKA reporter, AKAR3, showing a larger dynamic range of PKA BindR.
Figure 8:
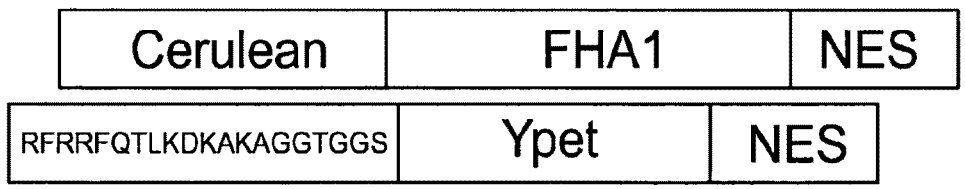
FIG. 8. Domain structure of a PKC BindR and its response in living cells.
Figure 8:
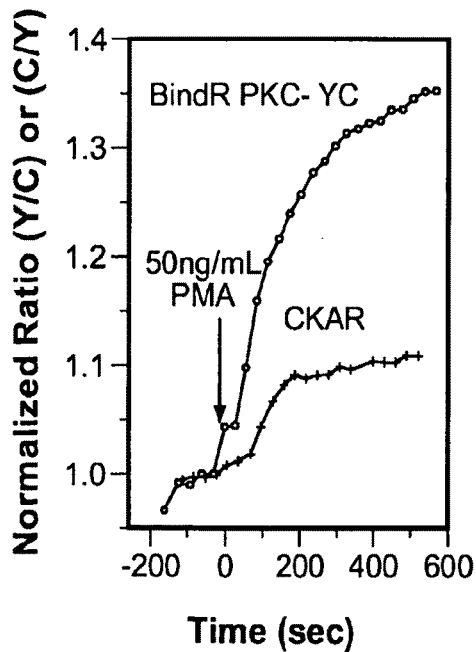

To test the functionality of BindR PICA and BindR PKC, FHA1 was tagged at its N-terminus with the cyan fluorescent protein (CFP) Cerulean and the substrates were C-terminally tagged with the yellow fluorescent protein (YFP) Ypet, generating BindR-PKA-YC and BindR-PKC-YC. Constructs were then co-expressed in 1205-Lu cells. After ~15 hours, cells were imaged as described above and treated with either the transmembrane adenylyl cyclase agonist Forskolin (Fsk) or the diacylglycerol mimetic phorbol myristate acetate (PMA). In the case of BindR-PKA-YC, Fsk induced an increase in yellow/cyan emission ratio of approximately 60%, and PMA caused an increase of approximately 30% from BindR-PKC-YC. See FIG. 7 and FIG. 8.

Example 3

Akt Activity Reporter

Materials

PDGF, Phorbol 12-Myristate 13-Acetate (PMA), forskolin, Calyculin A, methylated β-cyclodextrin (MβCD) and LY294002 were from Sigma. SH-5 was from Calbiochem. Restriction enzymes and the Taq polymerase were from NEB. MitoTracker, T4 ligase and Lipofectamine 2000 were from Invitrogen. The oligonucleotide primers were synthesized by Integrated DNA Technologies (Coralville, Iowa).

Construction of AktAR Constructs

Each AktAR construct was generated with a fluorescent protein pair sandwiching FHA1 domain and the substrate region. There is one linker region on each side of the substrate: AGKPGSGEGSTKGLVD (SEQ ID NO:29) on the left side and GGTGGSEL (SEQ ID NO:30) on the right side). Different variants of cyan and yellow fluorescent proteins, Cerulean, circularly permutated variants of Venus (K156, E172, L194, A228) and YPet were subcloned to the construct to replace corresponding CFP or YFP. The threonine in the phosphorylation motif was mutated to an alanine to create AktAR-T/A by PCR. All of the constructs were generated in pRSET B then subcloned to the mammalian expression vector pCDNA 3'.

Construction of Targeted AktAR

All of the targeting tags were subcloned to AktAR from targeted A Kinase Activity Reporter (AKAR) (Allen & Zhang, Biochem Biophys Res Commun. 2006, 22; 348(2): 716-21). Two plasma membrane targeted AktAR, PM(Lyn)-AktAR and AktAR-PM(CAAX), were generated by addition of the N-terminal portion of Lyn kinase gene at the 5' end and CAAX tag at the 3' end of AktAR, respectively. Nuclear localization was achieved by a C-terminal nuclear localization signal (NLS) tag (PKKKRKVEDA, SEQ ID NO:31). The targeting motif from DAKAP1a was used to target AktAR to the outer membrane of mitochondria.

Cell Culture and Transfection

NIH 3T3 cells were used in all experiments. The cells were plated on sterilized glass coverslips in 35-mm dishes and were grown to 40% confluency in Dulbecco's modified Eagle's medium (10% FBS) at 37° C. with 5% $CO_2$. Cells were transfected with Lipofectamine (Invitrogen) then serum-starved for 24 h before imaging.

Cell Imaging

NIH 3T3 cells were washed once with Hanks' balanced salt solution (HBSS) buffer and imaged in the dark at room temperature. Images were acquired on a Zeiss Axiovert 200M microscope with a cooled charge-coupled device camera, as described in Ananthanarayanan, 2005. Dual emission ratio imaging used a 420DF20 excitation filter, a 450DRLP dichroic mirror, and two emission filters. For CFP and YFP, 475DF40 and 535DF25 were used respectively. Exposure time was 50-500 ms. Images were taken every 20-30 s.

Imaging Data Analysis

Imaging data were analyzed with Metafluor 6.2 software (Universal Imaging, Downingtown, Pa.). Fluorescence images were background-corrected by deducting the background (regions with no cells) from the emission intensities of CFP or YFP. Traces before addition of drugs were normalized to 1.

Development of AktAR Reporters

Figure 9A:
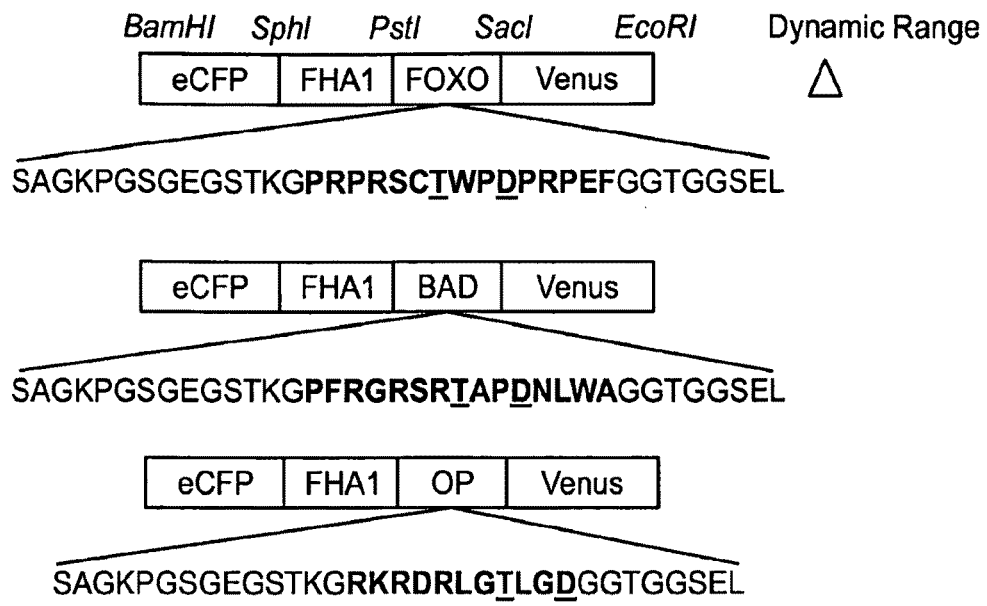
FIG. 9A-C. AktAR reporter constructs comprising a FHA1 domain and the substrate region flanked by a fluorescent protein pair. The dynamic range of each construct is indicated as following: Δ, 1~5%; ΔΔ, 5~10%; ΔΔΔ, 10~20%; ΔΔΔΔ, 20~30%; ΔΔΔΔΔ, 30~40%.

Improved Akt Activity Reporter (AktAR) were generated through systematic testing of different Akt substrates and fluorescent proteins. Three Akt phosphorylation motifs were used in the first round of AktAR evolution. Scansite showed the N-terminal Akt phosphorylation motifs of FOXO have the top scores as endogenous Akt substrates among a proteome-wide search. Akt phosphorylates FOXO1 at Ser-24 and Thr-256. SGK and DYRK1a phosphorylate Ser-319, Ser-322, Ser-325, and Ser-329 of FOXO1. Therefore, the FOXO1 Akt phosphorylation motif (Thr 24, PRPRSCTWPDPRPEF (SEQ ID NO:32), the phospho-acceptor threonine is shown in bold), together with the Akt substrate used in Aktus (PFR-GRSRTAPDNLWA (SEQ ID NO:33), and the phospho-acceptor threonine is shown in bold) the Akt substrate used in BKAR (RKRDRLGTLGD SEQ ID NO:34, the phospho-acceptor threonine is shown in bold), were used to engineer the first set of initial Akt activity reporters. The P+3 amino acid residue in every substrate motif was mutated to an aspartate to assist the FHA1 domain binding. The constructs were generated with the FRET pair ECFP and Venus flanking the FHA1 domain and the substrate region (FIG. 9A). The construct with Akt phosphorylation motif of FOXO1 showed an increase in yellow over cyan emission ratio of approximately 4% upon stimulation of PDGF (50 ng/ml), while the other two did not respond under the same conditions.

Figure 9B:
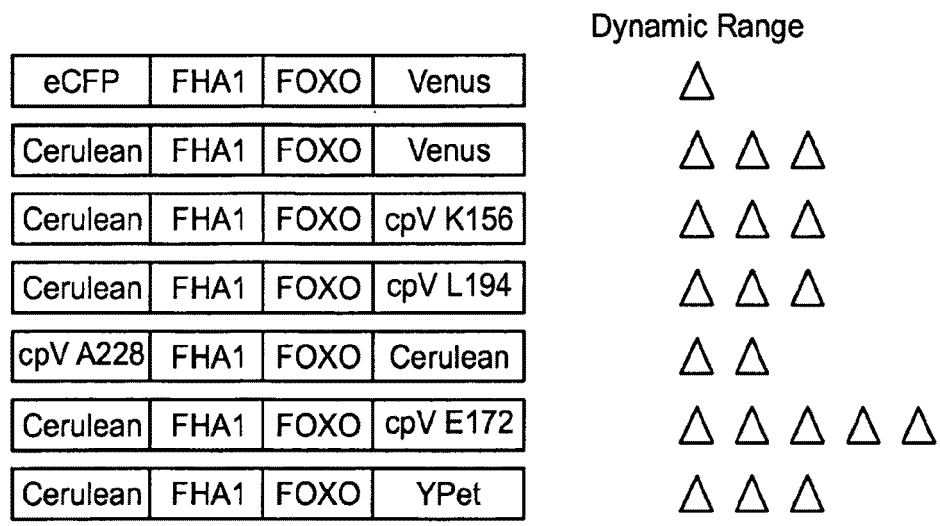

Because FOXO1 seemed to be the most promising substrate, the Akt phosphorylation motif of FOXO1 was used in the second round of AktAR evolution. The second round of AktAR evolution utilized different variants of cyan and yellow fluorescent protein to improve the dynamic range. By replacing the N-terminal ECFP with Cerulean, the dynamic range was increased to 12%. Four circularly permutated Venus variants, cpV K156, cpV E172, cpV L194 and cpV A228 were introduced to replace the wild type Venus (FIG. 9B). The optimized FRET pair CyPet-YPet has been shown to have improved FRET signal change (Nguyen, 2005 #35). Because CyPet did not fold properly, YPet was used to substitute the wild type Venus (FIG. 9B).

Figure 9C:
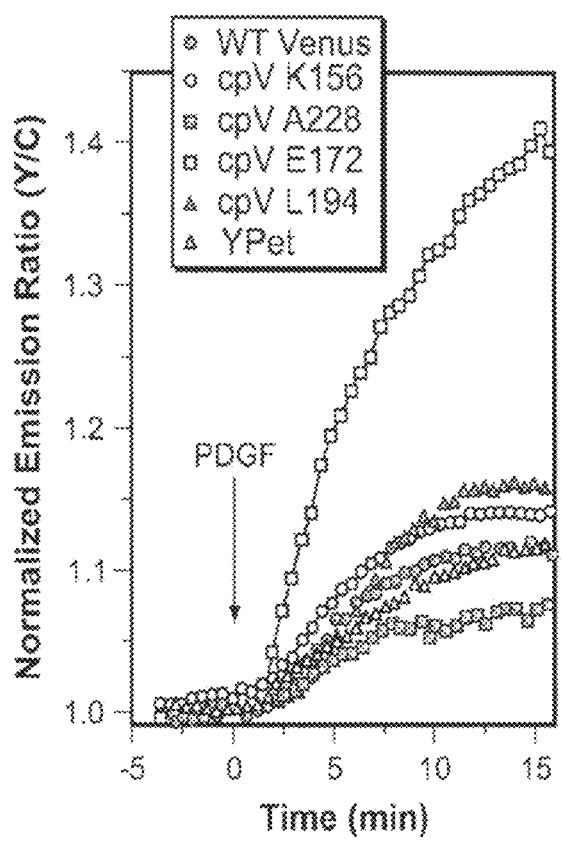

As shown in FIG. 9C, substitution with cpV K156, cpV L194, cpV A228 and YPet did not improve the dynamic range of the reporter, conversely, replacing of the wild type Venus with cpV E172 robustly increased the response to 38±4% (n=6). This could be due to the structural differences among the variants: N- and C-terminus of cpV K156 and cpV L194 are on the same face of the β-barrel as the wild type, while E172 is on the different face of the β-barrel, therefore cpV E172 creates a different orientation of the YFP.

AktAR showed an improved dynamic range five times that of BKAR upon stimulation of PDGF in serum-starved NIH3T3 cells. Also, phosphorylation of the threonine in the substrate motif of BKAR results in a decrease of FRET ratio (cyan emission over yellow emission), while phosphorylation of AktAR leads to an increase of FRET ratio, which rules out the possibility that the observed FRET ratio is partially due to the photo bleaching of YFP during the experimental process.

Cellular Response and Specificity of AktAR

Figure 10A:
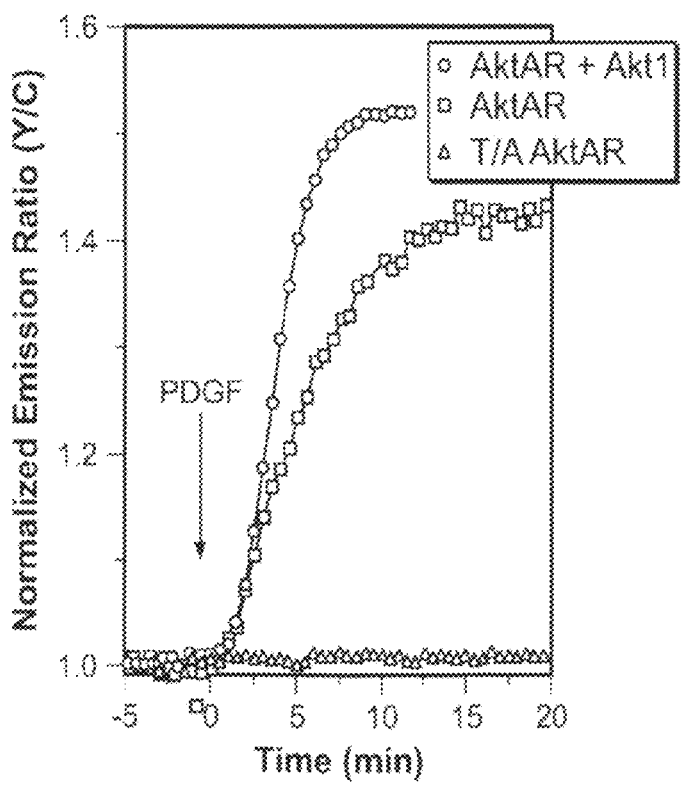
FIG. 10A-B. Graphs demonstrating cellular responses of AktAR.

To determine the effects of overexpression of Akt1 on the response of AktAR, overexpressed Akt1 activity was monitored in serum-starved NIH3T3 cells. FIG. 10A shows overexpression of AktAR with wild type Akt1 increased the dynamic range of AktAR to 52% upon treatment of PDGF (50 ng/ml). To determine if Akt phosphorylation of the threonine in the substrate motif in AktAR results in the FRET ratio change, the AktAR-T/A mutant, in which the threonine in the substrate motif was mutated to an alanine, was generated. The mutant failed to respond to PDGF stimulation in serum-starved NIH3T3 cells (FIG. 10A). Taken together, the data indicate that phosphorylation of the predetermined threonine caused AktAR's FRET change.

Figure 10B:
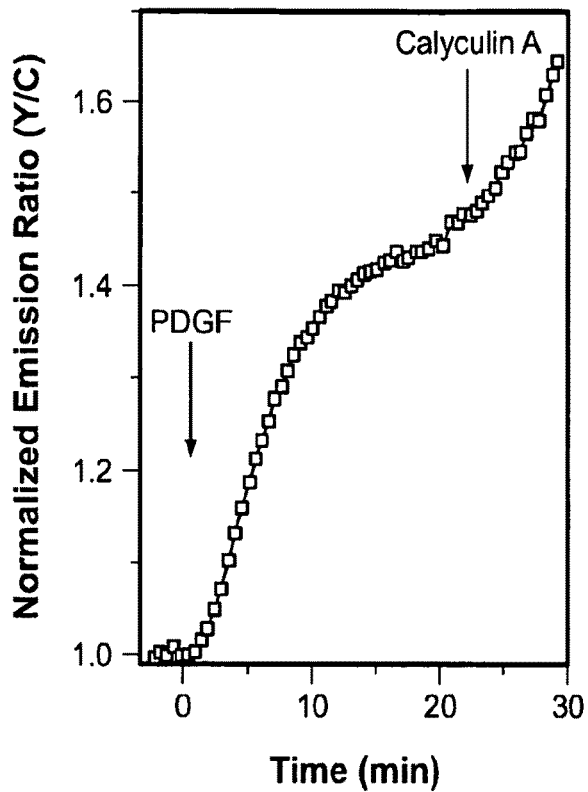

Several serine/threonine phosphatases, including PP2A, regulate Akt activity in vivo by dephosphorylating Akt. Calyculin A, an inhibitor specific for the serine/threonine phosphatases PP1 and PP2A, was used to test the full dynamic range of AktAR. FIG. 10B shows that suppressing phosphatase activities substantially increased the response of AktAR upon addition of 5 nM Calyculin A. The data revealed that most Akt activity can be detected by AktAR upon stimulation of PDGF, and parts of Akt activity can only be detected with the inhibition of phosphatases, indicating that dephosphorylation of either Akt or the reporter itself by phosphatases.

Figure 11A:
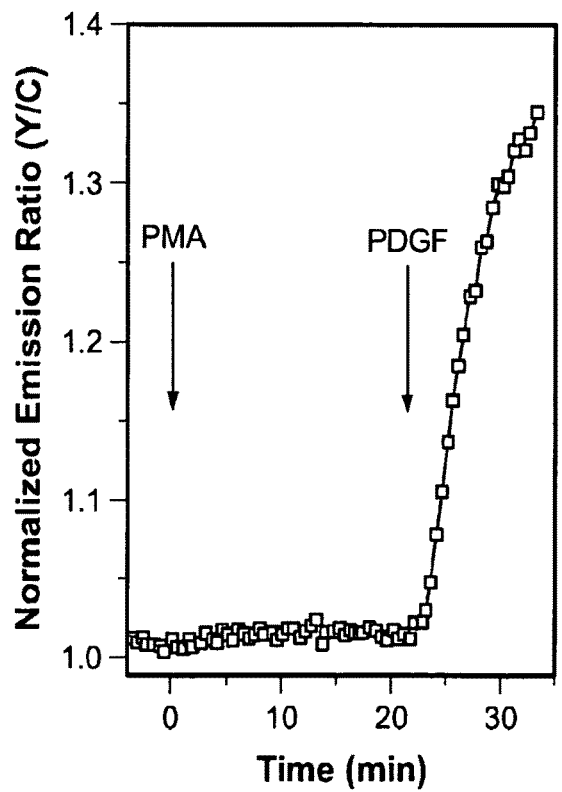
FIG. 11A-E. Graphs demonstrating the specificity of AktAR in vivo.
Figure 11B:
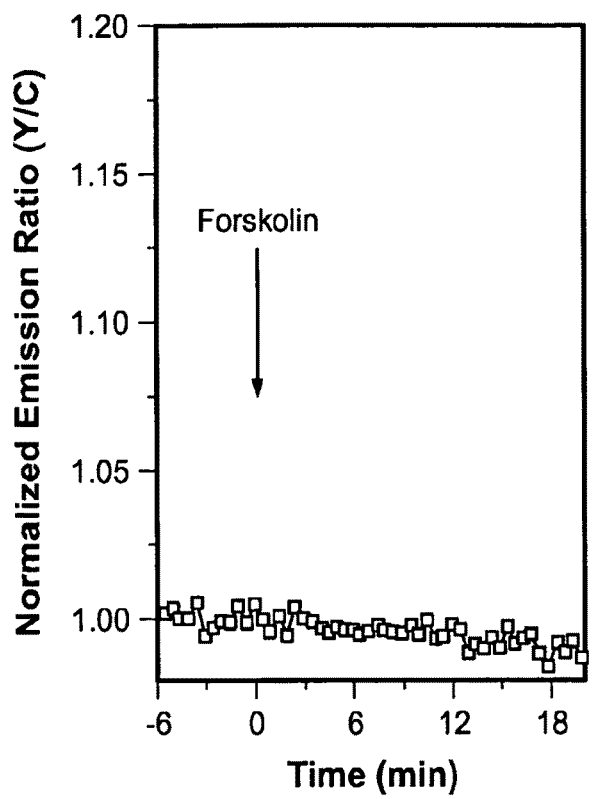

The ability of AktAR to detect the activities of two other AGC family kinases, PKC and PKA, was investigated to explore the specificity of AktAR in living cells. FIG. 11A shows that addition of 50 ng/ml PMA to activate PKC in serum-starved NIH3T3 cells did not induce any increase in the FRET ratio, while sequential treatment with PDGF caused a strong response, indicating that AktAR is not sensitive to PKC. Also, addition of 50 µM forskolin to activate PKA did not, induce any FRET ratio changes in serum-starved NIH3T3 cells, showing that AktAR is not responding to PKA (FIG. 11B).

Figure 11C:
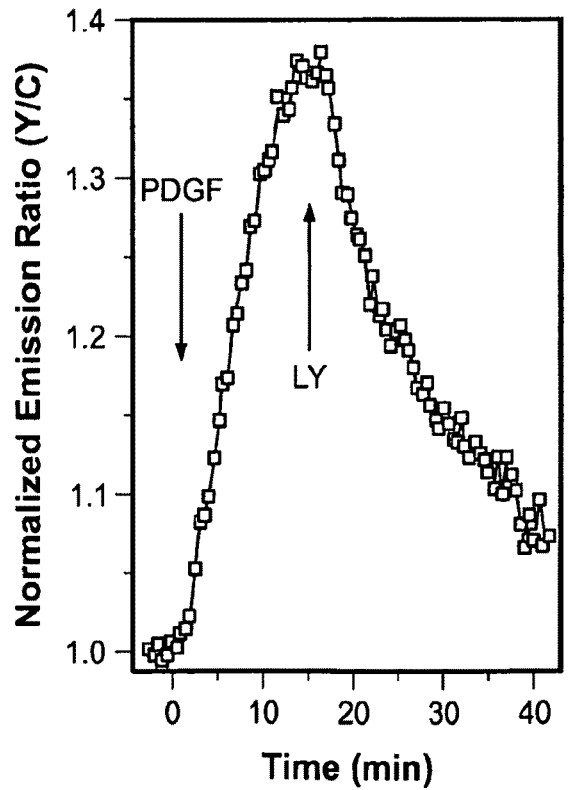

The reversibility of AktAR was also tested. LY294002 (20 µM) was used to inhibit PI3K, and hence downstream proteins, including Akt. The cells were treated with LY294002 after the PDGF stimulated response stabilized. Addition of LY294002 caused a decrease of FRET ratio (FIG. 11C). The data reveals that AktAR is reversible and specific for the activation of PI3K pathway. AktAR showed slower kinetics than BKAR did upon addition of LY294002. This could indicate AktAR is more resistant to phosphatase action than BKAR.

Figure 11D:
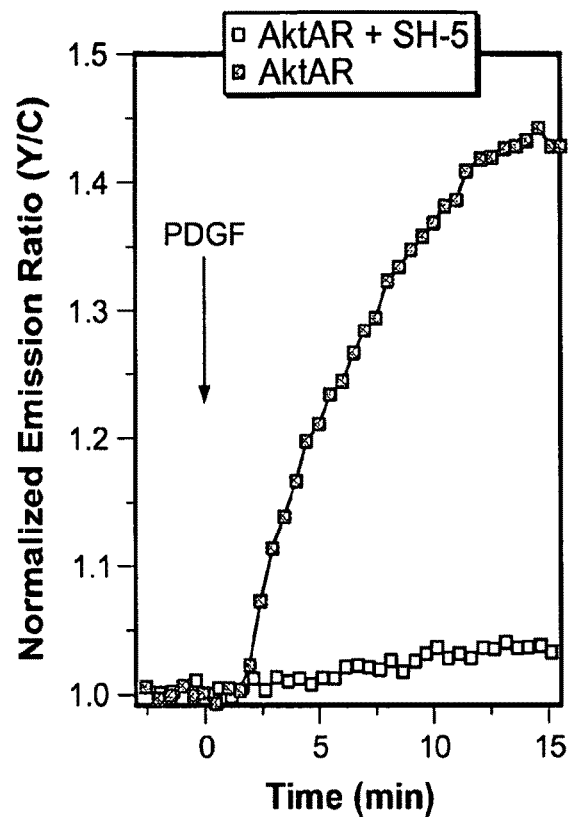

To determine if AktAR is specific for Akt, SH-5, a phosphatidylinositol analog that specifically inhibits Akt was used. NIH3T3 cells were transfected with AktAR then serum-starved. The cells were pre-incubated with 6 µM SH-5 in HBSS buffer before imaging. AktAR did not show substantial response upon treatment of PDGF in such conditions (FIG. 11D). The data confirm that AktAR is specific to Akt activation.

Figure 11E:
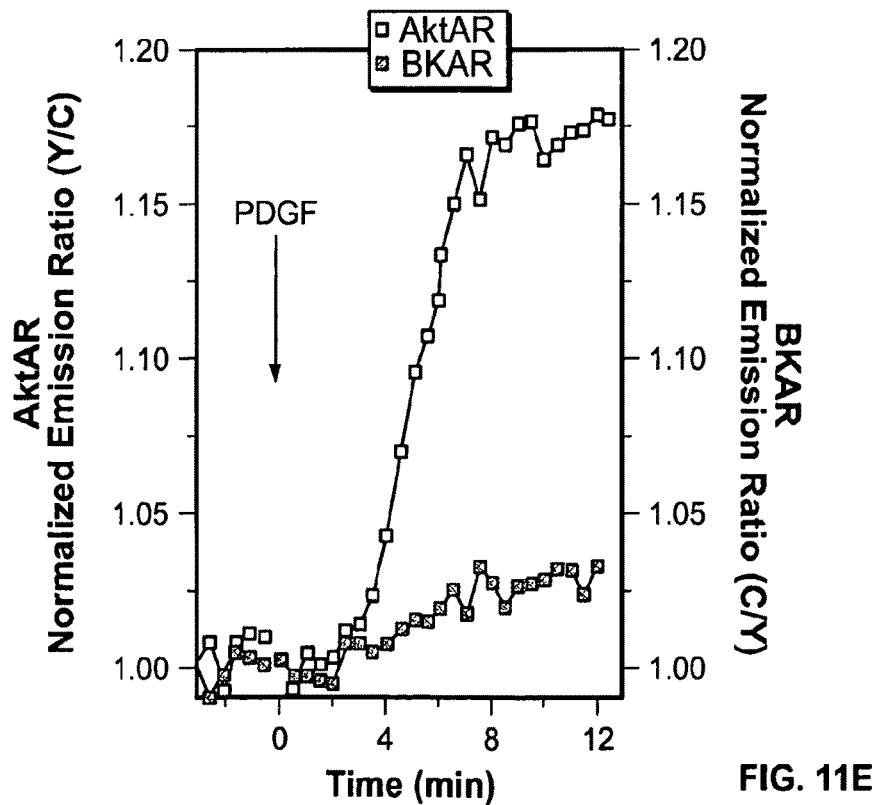

As a highly sensitive reporter, the ability of AktAR to detect Akt activity was also studied in un-starved NIH3T3 cells. As shown in FIG. 11E, AktAR was able to report endogenous Akt activity upon stimulation of 50 ng/ml PDGF in un-starved NIH3T3 cells, with a dynamic range of approximately 17%. BKAR has a response of about 3% under the same condition (FIG. 11E). The great sensitivity of AktAR provides a unique tool to investigate the effect of serum starvation on different cellular events.

Membrane Targeting of AktAR

To understand regulation and functional roles of Akt at different cellular membrane locations, AktAR was targeted to the lipid rafts and non-raft regions of the plasma membrane, as well as the mitochondrial outer membrane.

Akt Signaling at the Mitochondrial Outer Membrane

Figure 12A:
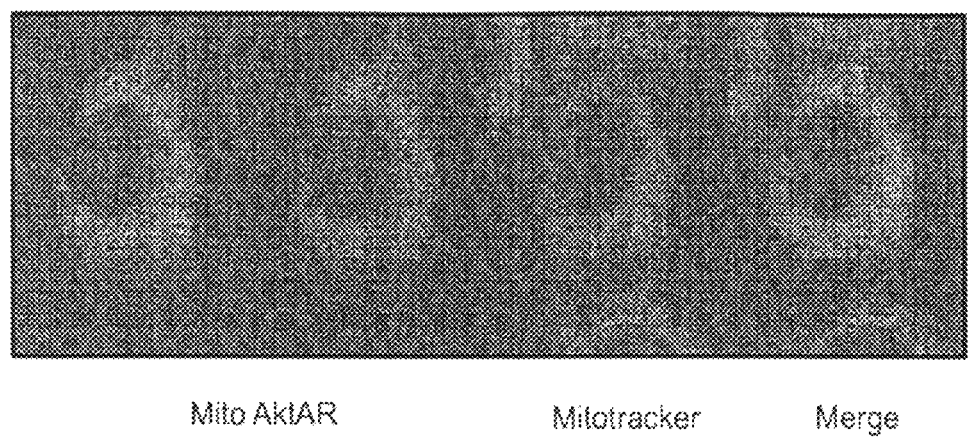
FIG. 12A-C. Akt Signaling at the Mitochondrial Outer Membrane.
Figure 12B:
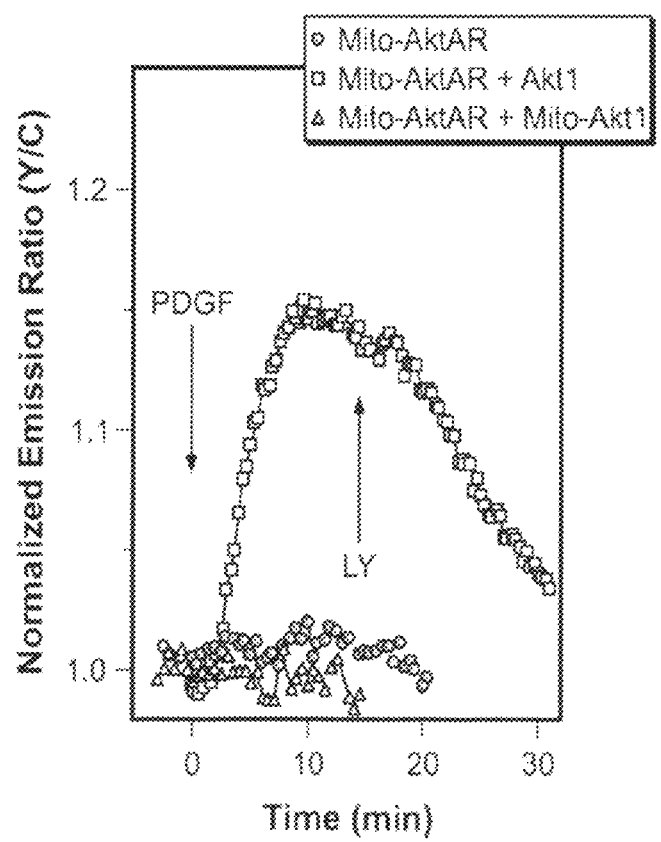

It has been known that Akt has several mitochondrial substrates. However, mitochondrial outer membrane targeted Aktus did not report any Akt activity upon growth factor stimulation in the presence of overexpressed Akt1 (Sasaki, 2003). In order to study Akt activity at this location, AktAR was targeted to the outer membrane of mitochondria with a DAKAP1a tag engineered at the N-terminus of the protein (FIG. 12A). Mito-AktAR was overexpressed in serum-starved NIH3T3 cells. Interestingly, no Akt activity was detected by Mito-AktAR upon stimulation of PDGF (FIG. 12B). Treatment with Calyculin A did not recover any Akt activity either (FIG. 12C), indicating that the null response is not due to suppression of Akt activity by phosphatases. In addition, the PI3K inhibitor, LY294002, was not able to decrease Akt activity in serum-starved NIH3T3 cells, suggesting that basal activity of Akt is undetectable. In summary, no basal, PDGF-stimulated, or phosphatase-suppressed endogenous Akt was detected at this location. It is possible that the extremely low activity of Akt at the mitochondrial outer membrane cannot be detected by Mito-AktAR.

To further study Akt activity at the mitochondrial outer membrane, we coexpressed Mito-AktAR with mCherry-Akt1 in serum-starved NIH3T3 cells. Mito-AktAR showed a 15% response upon stimulation of PDGF in the presence of overexpressed Akt1. The response can also be reversed with the treatment of LY294002 (FIG. 12B). Addition of Calyculin A further increased the response (FIG. 12C), indicating that the activity of overexpressed Akt is partially inhibited by phosphatases at this location. The low activity of Akt at the mitochondrial outer membrane requires a robust system to be monitored. This observation showed that active Akt can be detected at the mitochondrial outer membrane upon stimulation of PDGF, though it is unclear if Akt was activated at the compartment or if active Akt was transferred to the region after gaining activity at other subcellular locations.

Figure 12C:
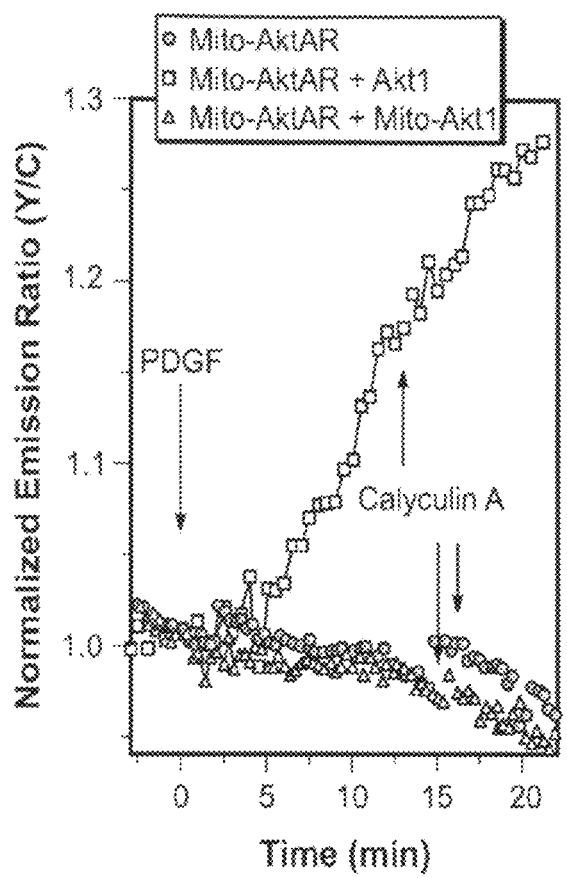

To answer this question, Mito-AktAR was overexpressed with the mitochondrial outer membrane targeted mCherry-Akt1 Mito-AktAR failed to detect any Akt activity in the presence of Mito-mCherry-Akt1 in this compartment (FIG. 12B). Addition of LY294002 did not induce any decrease of FRET ratio of Mito-AktAR in serum-starved NIH3T3 cell. Moreover, treatment with Calyculin A failed to activate mitochondrial outer membrane-bound Akt (FIG. 12C). The data here indicate Akt cannot be activated at the mitochondrial outer membrane in response to PDGF.

Akt Signaling at the Plasma Membrane

There are multiple microdomains on the plasma membrane. Among them, the cholesterol rich, detergent-resistant microdomains, lipid rafts, have been suggested as important signaling platforms (Hancock, *Nat. Rev. Mol. Cell. Biol.* 4, 373-84, 2003). Akt activity at lipid rafts versus non-raft regions of the plasma membrane has only recently been evaluated (Adam et al., *Cancer Res* 67, 6238-46, 2007). To better understand Akt signaling at these locations, Akt activity at the plasma membrane microdomains was investigated with two plasma membrane targeted constructs, PM(Lyn)-AktAR and AktAR-PM(CAAX). The N-terminal portion of Lyn kinase gene directs AktAR to the lipid rafts through myristoylation and palmitoylation, while the C-terminal CAAX along with a poly lysine motif, adapted from K-ras, anchors AktAR to the non-raft plasma membrane (Zacharias et al., *Science* 296, 913-16, 2002).

Figure 13A:
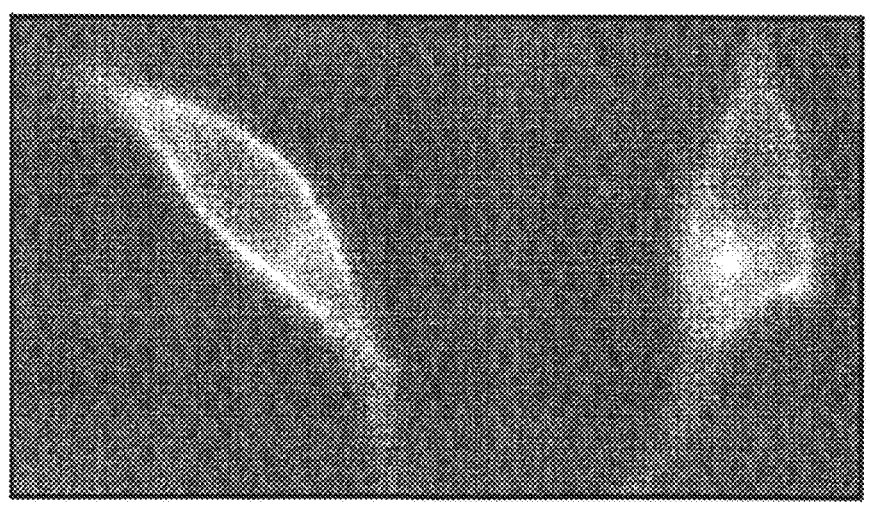
FIG. 13A-C. Akt Signaling at the Plasma Membrane.
Figure 13B:
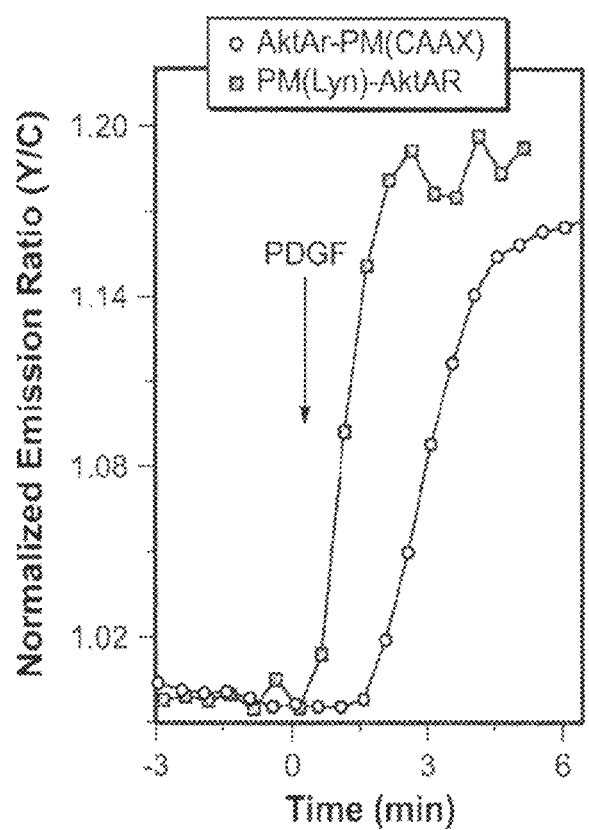

NIH3T3 cells were transiently transfected with either PM(Lyn)-AktAR or AktAR-PM(CAAX) then serum-starved for 24 hours (FIG. 13A). As shown in FIG. 13B, PM(Lyn)-AktAR and AktAR-PM(CAAX) both had faster kinetics than diffusible AktAR upon PDGF stimulation. Interestingly, these two constructs showed different dynamic ranges and kinetics upon stimulation. The t1/2 of PM(Lyn)-AktAR was approximately three times smaller than that of AktAR-PM (CAAX), indicating Akt activity is differentially regulated at these two locations.

Figure 13C:
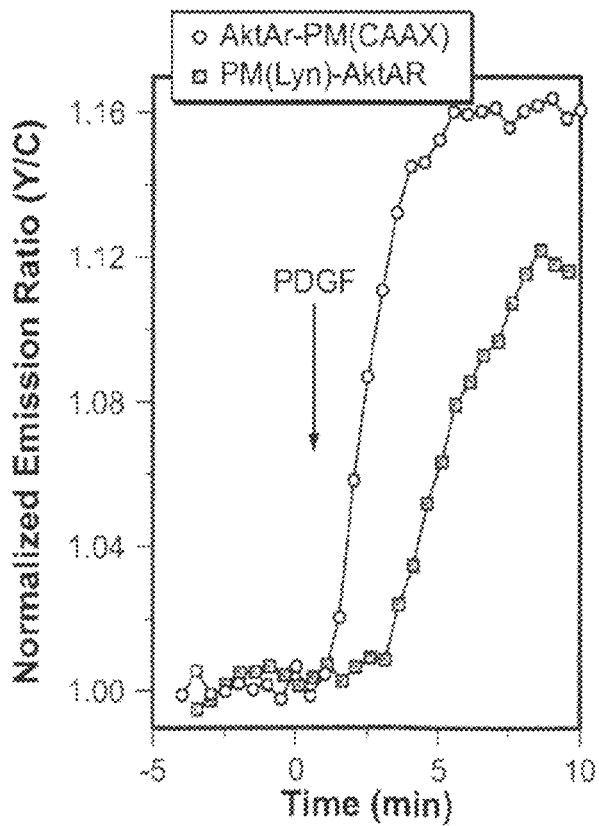

It has been shown Akt activation is inhibited upon disruption of membrane rafts (Arcaro et al., *Cell Signal* 19, 1081-92, 2007). We further investigated Akt activity in these two plasma membrane microdomains by membrane cholesterol depletion. NIH3T3 cells overexpressing either PM(Lyn)-AktAR or AktAR-PM(CAAX) were pre-incubated with 5 mM MβCD for 30 min, then stimulated with PDGF (FIG. 13C). AktAR-PM(CAAX) had similar response patterns upon stimulation of PDGF with or without pre-incubation of MβCD, while the kinetics and dynamic range of PM(Lyn)-AktAR underwent dramatic changes. Disruption of membrane rafts induced a delayed response and reduced dynamic range of PM(Lyn)-AktAR. Interestingly, the kinetics of PM(Lyn)-AktAR was even slower than that of AktAR-PM (CAAX) with pre-incubation of MβCD (FIG. 13C). This could indicate AktAR-PM(CAAX) is also located at some specific plasma membrane microdomains instead of evenly distributed on the non-raft regions.

In summary, use of the newly developed genetically encodable fluorescent indicator for detection of endogenous Akt activity, AktAR, reveals that Akt activity is differentially regulated at cellular membrane compartments. Membrane targeted versions of AktAR revealed that Akt is first activated on the membrane, possibly the lipid rafts. Disruption of membrane rafts slowed Akt activation at the lipid rafts, without affecting that at the non-raft region. Aid activity is low at the mitochondrial outer membrane, and Akt cannot be activated at this compartment by PDGF stimulation.

AktAR Detects Mitochondrial Outer Membrane Bound Active Akt

The physiological functions of Akt at the mitochondria are crucial but have not yet been elucidated. One Akt substrate, Bad, promotes apoptosis by complexing with Bcl-2 or Bcl-XL. The complex then translocates to the mitochondrial outer membrane. Active Akt initiates the formation of BAD:14-3-3 complex by phosphorylating BAD at Ser-136, therefore inhibiting cell apoptosis. Akt has been taken as an important mediator not only in anti-apoptotic pathways, but also in cell metabolism. Another Akt target at the mitochondria, mitochondrial hexokinase, controls glucose metabolism by phosphorylating glucose to glucose-6-phosphate. Mitochondrial hexokinase also has increased activity in many tumors, and its activity is related to tumor growth rates.

Aid can be detected throughout the mitochondria in SH-SY5Y cells (Bijur et al., *J. Neurochem.* 87(6), 1427-35, 2003). Studies showed that growth factors induce Akt translocation to the mitochondria (Bijur, 2003). In previous investigations, Aktus was targeted to the mitochondrial outer membrane. Unfortunately, the construct failed to detect any active Akt upon growth factor stimulation in the presence of overexpressed Akt1 at the outer membrane of mitochondria. It only showed Akt activity with overexpression of both Akt and the estrogen receptor at this location in CPAE cells. Here we successfully detected Akt activity at the mitochondrial outer membrane with Mito-AktAR upon stimulation of the growth factor PDGF.

Immunoblot analysis revealed that Akt is predominantly cytosolic. The expression level of Akt in the mitochondria is fairly low (Bijur, 2003). Trypsin digestion of mitochondria indicated that Akt is mostly located within the mitochondria in SH-SY5Y cells. (Bijur, 2003). Here we showed that endogenous Akt activity at the mitochondrial outer membrane in NIH3T3 cells is actually too low to be detected by AktAR. Active Akt can only be detected in the presence of overexpressed Akt1 upon stimulation of PDGF. Furthermore, Akt cannot be activated at this location in response to PDGF. It seems that Akt is phosphorylated and activated at other cellular locations, such as plasma membrane, then activated Akt translocates to the mitochondrial outer membrane to play its physiological roles.

Akt Activity is Differentially Regulated at the Plasma Membrane Microdomains

The observation of rapid activation of Akt at the plasma membrane is consistent with the established models of Akt activation, where Akt is phosphorylated and activated at the plasma membrane following PI3K and PDK1 activation. More importantly, we used two plasma membrane targeted AktAR constructs, PM(Lyn)-AktAR for membrane raft targeting and AktAR-PM(CAAX) for non-raft region targeting, to investigate Akt activation mechanism on the microdomains of plasma membrane. Lots of studies have been done on the microstructure of the plasma membrane. The plasma membrane is considered to be a complex consisting of many microdomains. They can be roughly divided to lipid rafts and non-raft regions. Regulation of Akt activity at different microdomains of the membrane is critical yet intriguing. It has been indicated that raft-associated Akt could be an important determinant of oncogenicity (Adam et al., *Cancer Res.* 67, 6238-46, 2007). However, the nature of Akt regulation at the membrane microdomains remains undefined. Recent data has shown that in small cell lung cancer (SCLC) cells, the activation of distinct PI3K isoforms through raft associated Src kinases leads to activation of Akt, and raft disruption inhibits Akt activation (Arcaro et al., *Cell Signal* 19, 1081-92, 2007). The distinct functions of lipid raft and non-raft associated Akt has also been investigated in the human prostate cancer cell line, LNCaP. The data suggested different substrate preference between these two Akt pools (Adam, 2007).

Here we observed kinetic and amplitude differences between the responses from these two plasma membrane targeted reporters, indicating Akt activity is differentially regulated at these two locations. Akt is possibly first activated at the lipid rafts, regardless of relatively low amount of total Akt detected on this microdomain (Arcaro, 2007; Adam, 2007). The Akt pool at the non-raft regions was phosphorylated slower than that at the lipid rafts, judging from the kinetics of these two. The difference of Akt activity among different plasma membrane regions provides valuable information towards understanding of Akt regulation of cholesterol metabolism, as well as the physiological functions of microdomains at the plasma membrane.

The plasma membrane has been known to be heterogeneous, with microdomains such as lipid rafts and non-raft regions. It is also likely that non-raft microdomains of the membrane are not homogeneous. It has been proposed that some micro-regions (e.g., an "acidic microdomain"), might exist on the non-raft microdomains. These acidic domains could be generated by polybasic proteins through electrostatic interactions (Hancock, 2003). In stead of located at the non-raft regions evenly, K-ras could specifically reside at these acidic regions (Hancock, 2003). In our experiments, the kinetics of PM(Lyn)-AktAR was slower than that of AktAR-PM(CAAX) after membrane cholesterol depletion by MβCD, indicating PM(Lyn)-AktAR and AktAR-PM (CAAX) might occupy different membrane microdomains even after lipid disruption. This could be because that AktAR-PM(CAAX) is located at the non-raft "acidic microdomain," while PM(Lyn)-AktAR is transferred from the lipid rafts to the general non-raft regions after cholesterol depletion.

In conclusion, we successfully generated a new genetically encoded FRET based Akt activity reporter, AktAR. Membrane targeted versions of AktAR provided new observation of Akt dynamics at the plasma membrane lipid rafts and non-raft regions, as well as the outer membrane of mitochondria. The use of AktAR in different biological systems can reveal detailed mechanisms of Akt signaling.

Example 4

MAP Kinase Reporters

Plasmid Construction

A JNK reporter was constructed by engineering a chimera of enhanced cyan fluorescence protein (ECFP, the significant mutations are as follows: K26R, F64L, S65T, Y66W, N146I, M153T, V163A and N164H), FHA1 phosphoaminoacid binding domain from Rad53p, a truncated form of JDP2 (amino acids 144-163) and citrine (an improved yellow fluorescence protein, the significant mutations are as follows: S65G, V68L, Q69M, S72A, T203Y and H231L). Schematically, the reporter comprises:

ECFP-FHA1-JDP2(144-163)-citrine

The forward primers (5' to 3') for the JNK reporter were:

```
                                           (SEQ ID NO: 35)
1: GAGTCAGAAGGCAACCCACTGCTCGAGCAGCTCGAGAAGAAGGGCGG
CACCGGCGGCAGCGAGCTCATGGTGAGCAAG;
and
                                           (SEQ ID NO: 36)
2: acgcGTCGACGACAGTGTCAAGACCCCCGAGGATGAAGGCAACCCAC
TGCTCGAGCAGC.
```

The reverse primer which recognizes the 3' end of citrine was:

```
GGCGGATTCTTACTTGTACAGCTCGTCCATGC.   (SEQ ID NO: 37)
```

The JNK reporter was constructed by two overlapping PCR reactions using citrine as the initial template. The first PCR reaction included primer 1 which hybridizes to the 5' end of citrine and incorporates a linker and Sac1 restriction digest site immediately before citrine. The second PCR reaction used primer 2 which hybridizes to the 5' end of the first PCR reaction and incorporates a Sal1 restriction digest site at the 5' end. Both PCR reactions used the reverse primer which includes an EcoR1 site.

PCR was performed using 50 ng of template, 300 nM of each primer, 500 nM of each of dNTPs, 2.5 Unit of Taq polymerase (Gibco) in PCR reaction buffer (Boehringer Mannheim). The standard PCR program was modified to accommodate reactions using long primers: 95° C. 5 min; [95° C. for 1 min, 40° C. for 1 min, 72° C. for 2.5 min]×2 cycles; [95° C. for 1 min, 43° C. for 1 min, 72° C. for 2.5 min]×4 cycles; [95° C. for 1 min, 45° C. for 1 min, 72° C. for 2.5 min]×4 cycles; [95° C. for 1 min, 52° C. for 1 min, 72° C. for 2.5 min]×14 cycles; 72° C. for 7 min; hold at 4° C. The amplified product was then purified using Qiagen gel purification kit and digested with Sal1 and EcoR1. The digested mixture was then purified using Qiagen PCR purification kit.

The Sal1-EcoR1 digested PCR product was ligated into Sal1-EcoR1 digested pRSET B vector (Invitrogen) containing the cDNA sequence for ECFP and FHA1. For mammalian expression, the construct was cloned into the vector pcDNA3 behind a Kozak sequence for mammalian expression.

Cell Culture

HeLa or HEK293 cells were plated onto sterilized glass coverslips in 35-mm dishes and grown to 50-90% confluency in low-glucose DMEM (10% FBS at 37° C. with 5% $CO_2$). Cells were transfected using calcium phosphate precipitation method. Briefly, 1 μg of DNA (purified using the Midiprep Kit from Qiagen), 8.2 μl of 2M $CaCl_2$ were diluted to a final volume of 100 μl with water and added dropwise to 100 μl of HBS. After 30 min incubation at room temperature, the mixture was added to the cells. For imaging, the cells were washed twice with HBSS buffer (20 mM Hepes, pH 7.4, 2 g/L D-glucose) and maintained in HBSS in the dark at room temperature.

Imaging

Cells were imaged in the dark at room temperature on a Zeiss Axiovert 200M microscope with a cooled charge-coupled device camera MicroMAX BFT512 (Roper Scientific, Trenton, N.J.) controlled by Metafluor 6.2 software (Universal Imaging, Downingtown, Pa.). Dual-emission ratio imaging used a 420DF20 excitation filter, a 450DRLP dichroic mirror, and two emission filters (475DF40 for ECFP and 535DF25 for citrine) alternated by a filter-changer Lambda 10-2 (Sutter Instruments, Novato, Calif.). Exposure time was 50-500 ms, and images were taken every 30 s.

Construction of JNK Reporters

Figure 14:
FIG. 14. Schematic of MAPK reporter design. Diagram of reporter design showing sequence of a JDP2-based substrate (SEQ ID NO:17) with the docking domain. The highlighted T represents the phosphoacceptor, Thr. (D) represents the mutation that was performed to facilitate binding to FHA1.

JNK regulates diverse biological processes by phosphorylation of a multitude of downstream substrates at Ser/Thr residues. FHA1 can bind to phosphothreonine containing proteins and prefers an aspartate at the +3 position. We therefore constructed chimeric proteins in which GFP variants that function as FRET pairs were genetically fused to FHA1 and truncated JDP2 (FIG. 14). Upon phosphorylation, interaction between FHA1 and the substrate will bring the two GFP variants into close proximity so that an increase in FRET correlates with phosphorylation. ECFP and citrine were used due to them functioning as an efficient FRET pair.

We used transcription factor JDP2 as a substrate peptide because it has been shown to be efficiently phosphorylated by JNK. It also contains a docking site for JNK that lies immediately c-terminal to the phosphoacceptor domain. This may be important in order to allow access of the phosphorylated substrate to FHA1. The +3 position relative to the phosphoacceptor was mutated to Asp to facilitate FHA 1 binding.

Expression and Behavior of JNK Reporters in Mammalian Cells

Figure 15A:
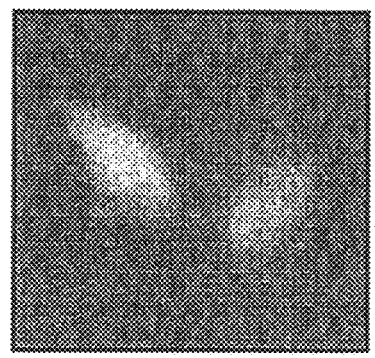
FIG. 15A-C. Response of reporter to known activators of JNK.
Figure 15B:
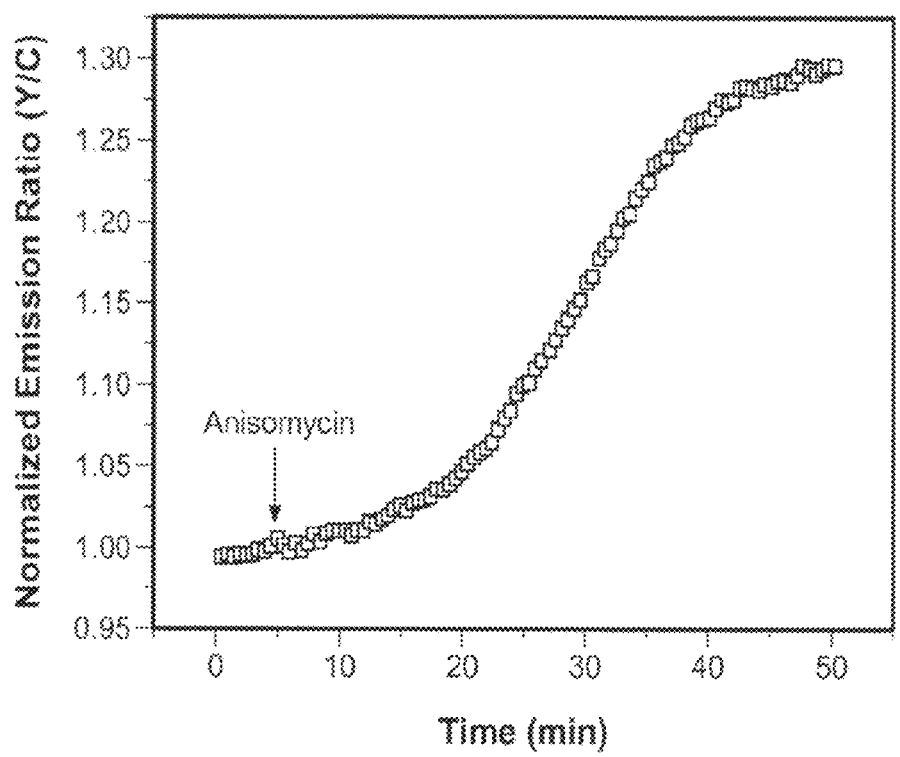
Figure 15C:
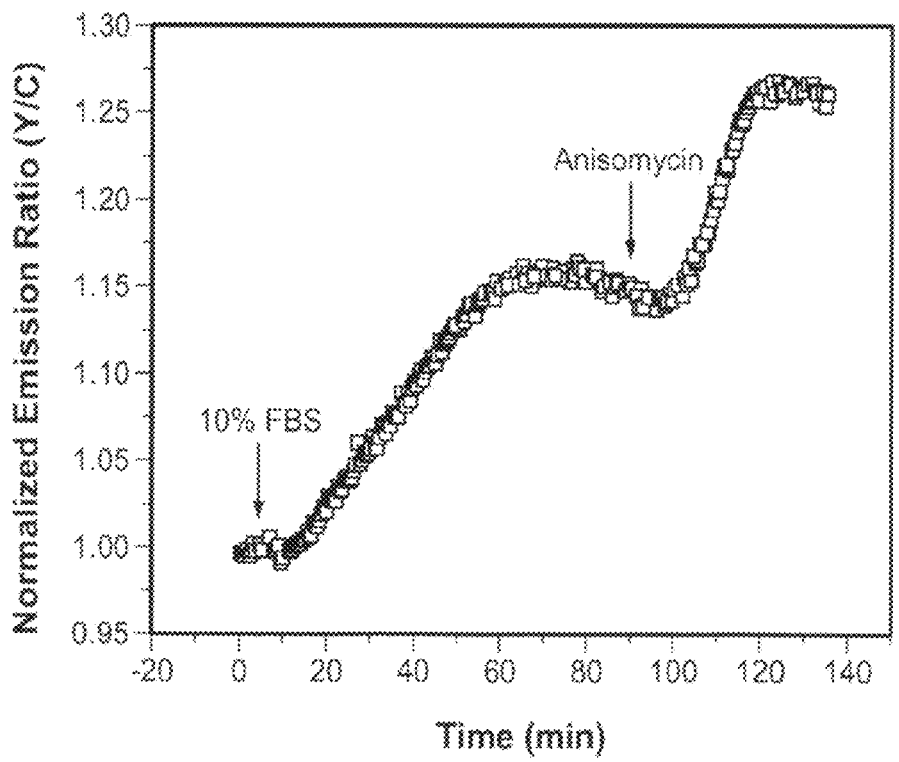

When the JNK reporter was transfected into HeLa cells, the fluorescence was uniformly distributed throughout the cell (FIG. 15A). To test the response of the reporter to a stressor, HeLa cells were treated with anisomycin, a protein translation inhibitor and a known potent activator of JNK (FIG. 15B). While there was an initial delay in response, the reporter exhibited an increase in emission ratio over time. The response took approximately 40-45 min to plateau at a maximum of 30%. Because JNK is also involved in cell proliferation and is activated by growth factors, the response of the reporter to FBS stimulation was tested (FIG. 15C). The reporter exhibited an increase in emission ratio in response to FBS with a maximum of 15%. Addition of anisomycin further increased the emission ratio to a maximum of 27%. This suggests that while FBS can lead to JNK activation, the amplitude of JNK activity is less than that of anisomycin treatment.

Figure 16A:
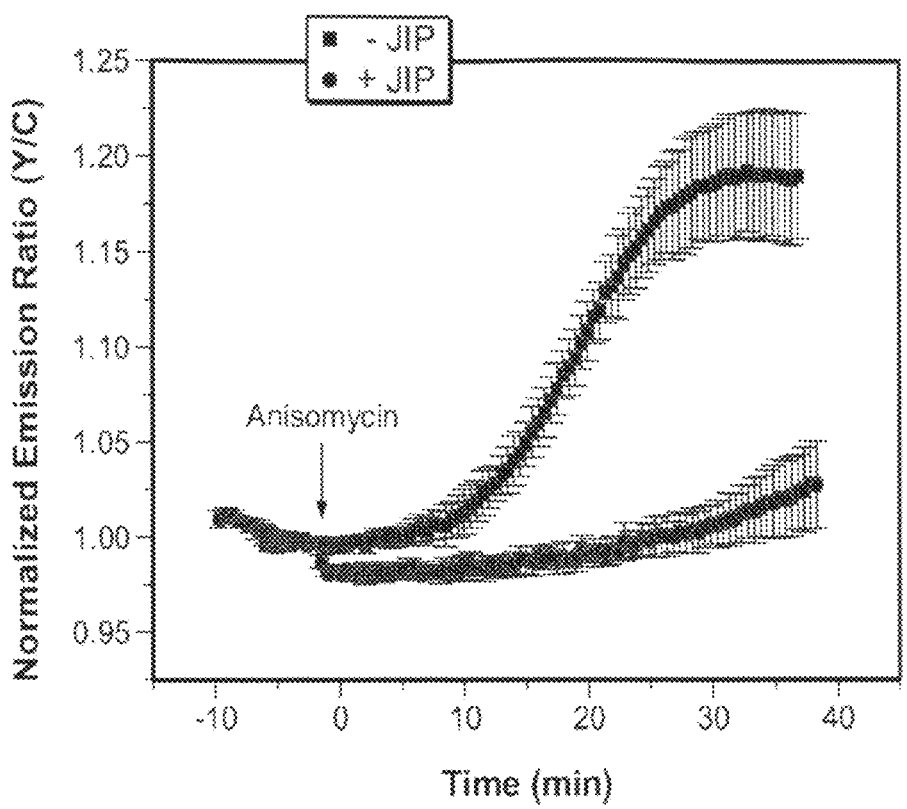
FIG. 16A-B. Characterization of a MAPK reporter.
Figure 16B:
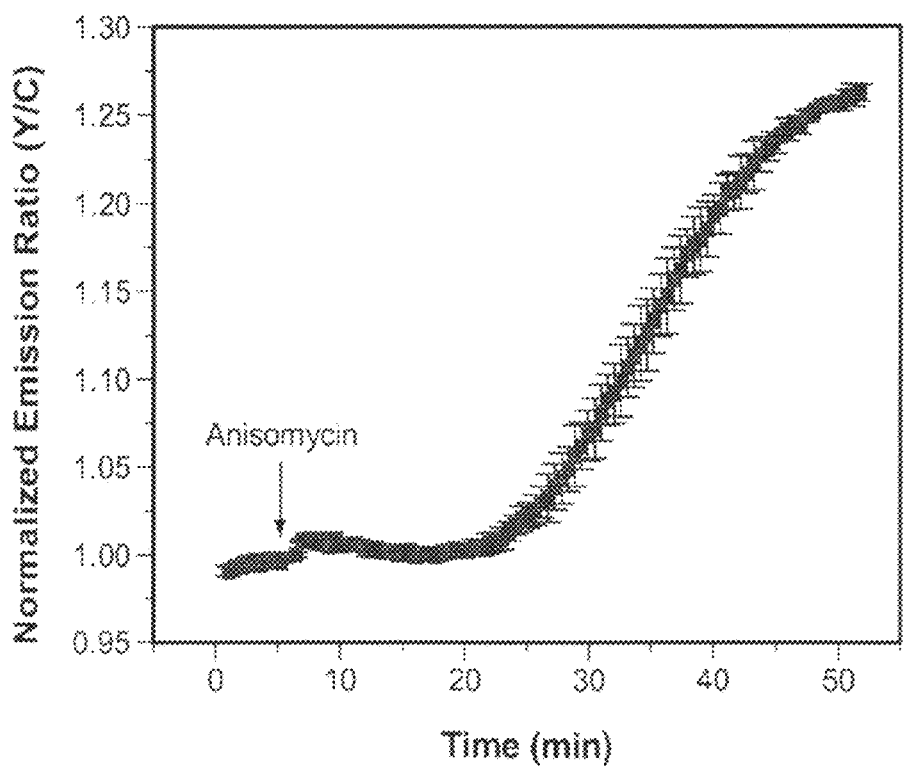
Figure 17:
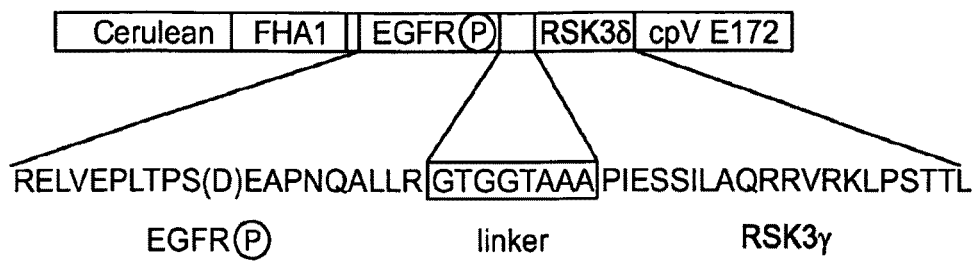
FIG. 17. Structure of ERK activity reporter (ERKAR) showing Substrate and Docking Site. Schematic showing substrate sequence from EGFR, docking domain from RSK3, and linker (SEQ ID NO:41). The highlighter T represents the phosphoacceptor, Thr. (D) represents the incorporated mutation to facilitate binding to FHA1.
Figure 18:
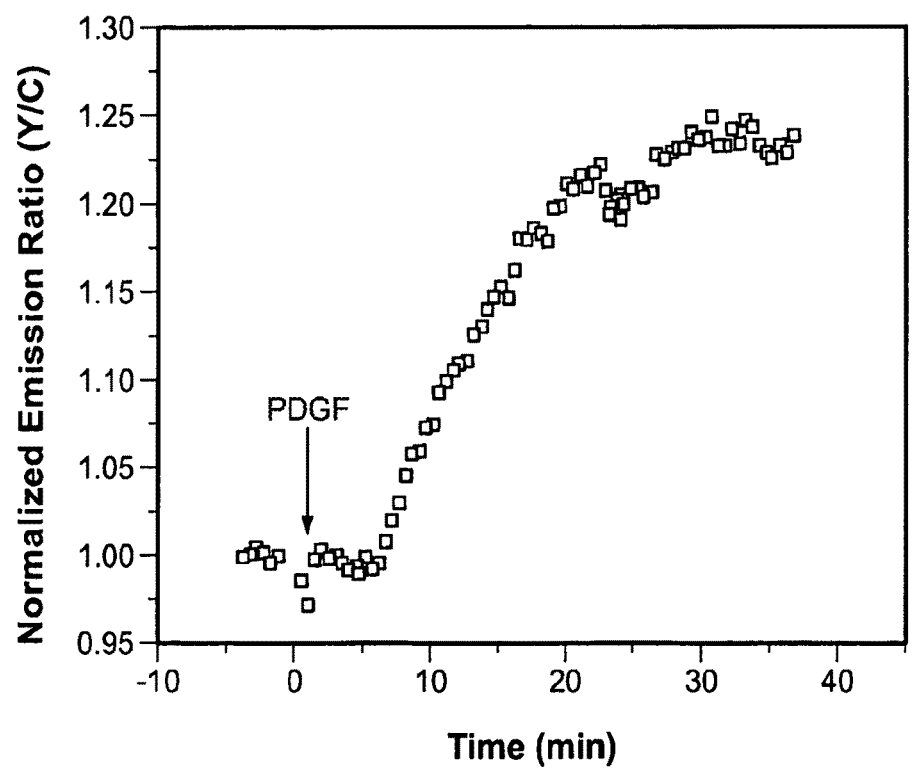
FIG. 18. Response of ERKAR to PDGF in NIH3T3 cells. NIH3T3 cells were transfected with ERKAR and serum-starved for 24 h. The transfected cells were then imaged on a stage warmer heated to 37° C. The cells were stimulated with 50 ng/ml of PDGF which elicited a 24% increase in emission ratio.

To test the specificity of the reporter, HeLa cells were co-transfected with the reporter and a fusion construct of mCherry with the docking (δ) domain from JIP1. This docking domain has been shown to directly interact with JNK and specifically inhibits JNK activity. Co-transfection of the reporter with mCherry-JIPδ led to a decrease in response with slower kinetics providing evidence that the reporter detects JNK activity (FIG. 16A). To test if the reporter responds to p38 MAPK, HeLa cells were pre-treated with SB203580 for 45 min then imaged in the presence of SB203580. Inhibiting p38 MAPK does not affect the response of the reporter to anisomycin, indicating that the reporter was not due to p38 activation.

A similar ERK reporter (ERKAR) was developed. The reporter is composed of Cerulean and circular permutated Venus (E172) as the FRET pair, FHA1 and an ERIC substrate. The ERK substrate is the substrate sequence from EGFR1 (RELVEPLTPSDEAPNQALLR; SEQ ID NO:38), a linker GTGGTAAA (SEQ ID NO:39), followed by the docking sequence from RSK3γ (PIESSILAQRRVRKLPSTTL; SEQ ID NO:40).

Example 5

Calcineurin Activity Reporter

Calcineurin, also known as protein phosphatase 2B, is a ubiquitously-expressed protein phosphatase whose activity is controlled by $Ca^{2+}$/calmodulin. Calcineurin is unique among the major protein phosphatases in that it is highly sensitive to fluctuations in the concentration of intracellular $Ca^{2+}$ ($[Ca^{2+}]_i$). As such, calcineurin plays an important role in coupling transient $Ca^{2+}$ signals to downstream cellular processes. In particular, calcineurin has been shown to modulate neuronal excitability during memory formation, to promote cardiac hypertrophy, and to drive T-cell activation. During the latter, calcineurin couples receptor-mediated $Ca^{2+}$ fluxes to cytokine production by altering the sub-cellular distribution of members of the nuclear factor of activated T-cells (NFAT) family of transcription factors.

Figure 20A:
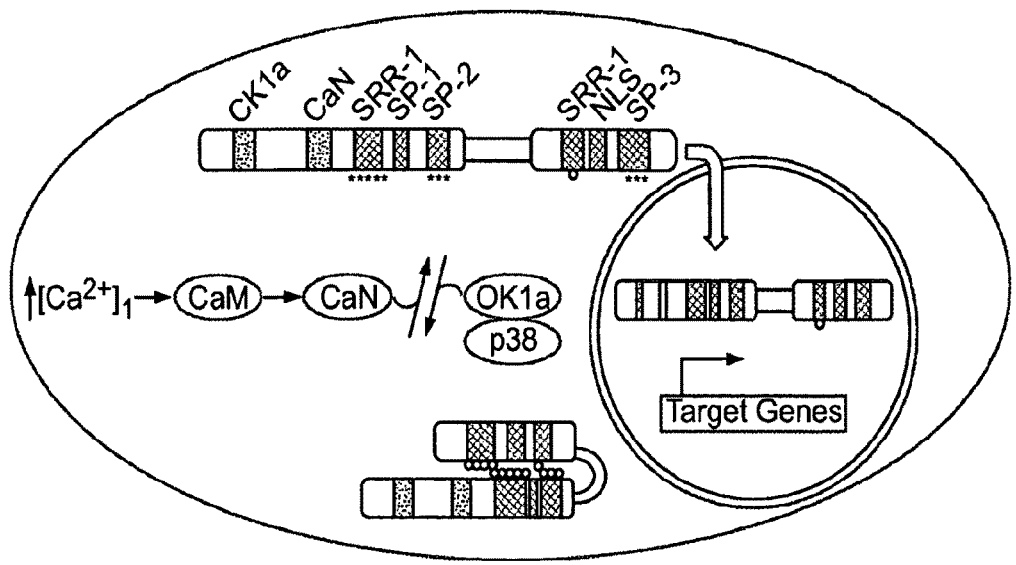
FIG. 20A-B. Calcineurin activity reporter based on nuclear factor of activated T-cells NFAT.

The distribution of NFAT family members depends upon the phosphorylation state of an N-terminal regulatory domain containing, among other regulatory motifs, a nuclear localization signal (NLS) and three highly-conserved serine-rich motifs termed SRR-1, SP2, and SP3 (FIG. 20A). In resting T-cells, multiple serine residues within the SRR-1 and SP motifs are phosphorylated by various kinases, including constitutively-active casein kinase 1α (CK1α phosphorylation of the serine-rich regions is believed to promote electrostatic interactions between negatively-charged phosphate groups and positively-charged residues located within the NLS. These interactions effectively mask the NLS and prevent NFAT from translocating into the nucleus. In response to elevated $[Ca^{2+}]_i$, calcineurin catalyzes dephosphorylation of the regulatory domain, inducing a conformational change that unmasks the NLS. Once its NLS is exposed, NFAT is able to migrate into the nucleus where it promotes the expression of several genes involved in the production of cytokines (FIG. 20A).

Figure 20B:
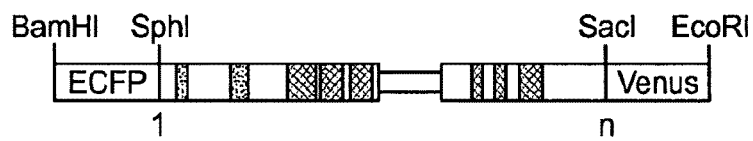

To develop a genetically-encoded reporter capable of monitoring the spatiotemporal dynamics of calcineurin activity within the cellular environment, we took advantage of the ability of calcineurin to specifically and efficiently dephosphorylate the regulatory domain of NFAT in response to increases in $[Ca^{2+}]_i$. To this end, truncated forms of the regulatory domain of the NFAT isoform NFAT1 were sandwiched between the enhanced cyan fluorescent protein (ECFP) and a circularly-permuted version of the yellow fluorescent protein, Venus, termed cpV(L194) (FIG. 20B). In this reporter design, NFAT1 serves as a molecular switch whose conformational state is regulated by calcineurin-mediated dephosphorylation. Meanwhile, ECFP and cpV(L194) act as a FRET pair to rapidly detect conformational changes in NFAT1.

Figure 25:
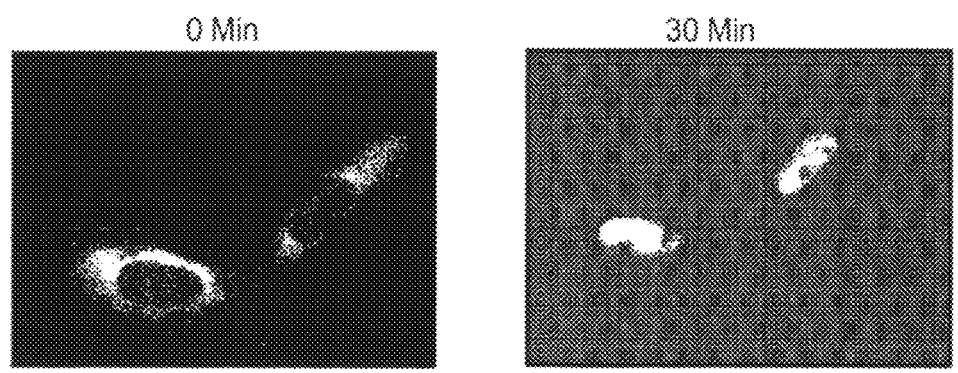
FIG. 25. ECFP-NFAT1(1-415) undergoes nuclear import following ionomycin treatment. The sub-cellular distribution of ECFP-NFAT(1-415) was measured before (first panel) and 30 minutes after (second panel) ionomycin treatment (1 µM).

In resting cells, the regulatory region of NFAT1 is expected to be hyperphosphorylated due to the action of cellular kinases such as CK1α and the mitogen activated protein kinase, p38. As a consequence, the reporter does not require the activation of additional kinases to put it into a "dephosphorylation-competent" state. This feature ensures that the cellular environment remains relatively unperturbed prior to $Ca^{2+}$ stimulation, reducing the potential for crosstalk with other signaling pathways which may otherwise complicate data interpretation. To test whether the fusion of GFP-like proteins to the N- and C-termini of the regulatory domain of NFAT1 impedes calcineurin-mediated dephosphorylation, a calcium-induced nuclear translocation assay was used to track the sub-cellular distribution of a protein chimera composed of ECFP fused to the N-terminus of the regulatory region of NFAT1. This construct, termed ECFP-NFAT(1-415), undergoes nuclear import following the addition of the $Ca^{2+}$ ionophore, ionomycin (FIG. 25). These results are consistent with previous data showing that the nuclear import of the regulatory domain proceeds in a manner similar to that of endogenous NFAT1, regardless of whether a fusion tag is attached to the N- or C-terminus of the protein.[15,20]

Figure 21:
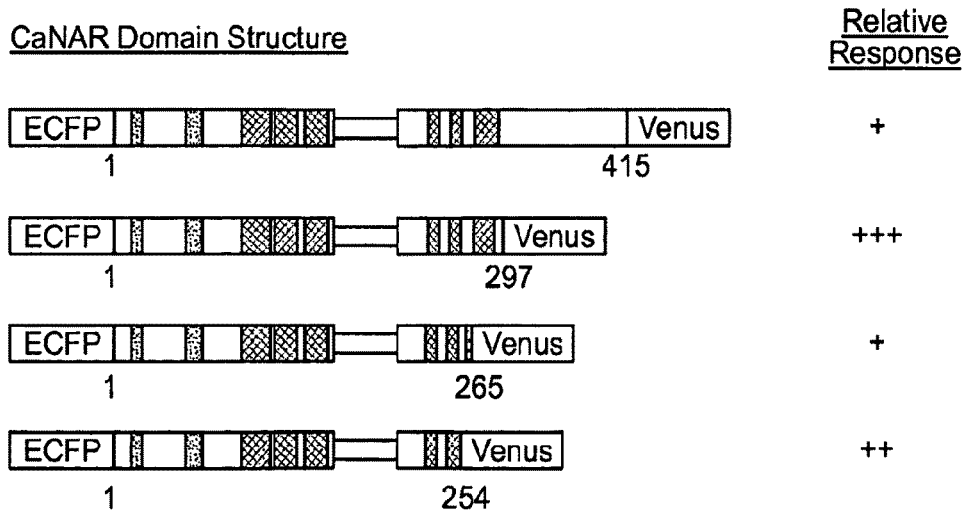
FIG. 21. Relative response of several test constructs. Constructs containing various-sized fragments of the regulatory domain of NFAT1 were transfected into HeLa cells, and changes in their emission ratios in response to ionomycin treatment were measured as a function of time. The relative response of each construct is indicated at the right.
Figure 26:
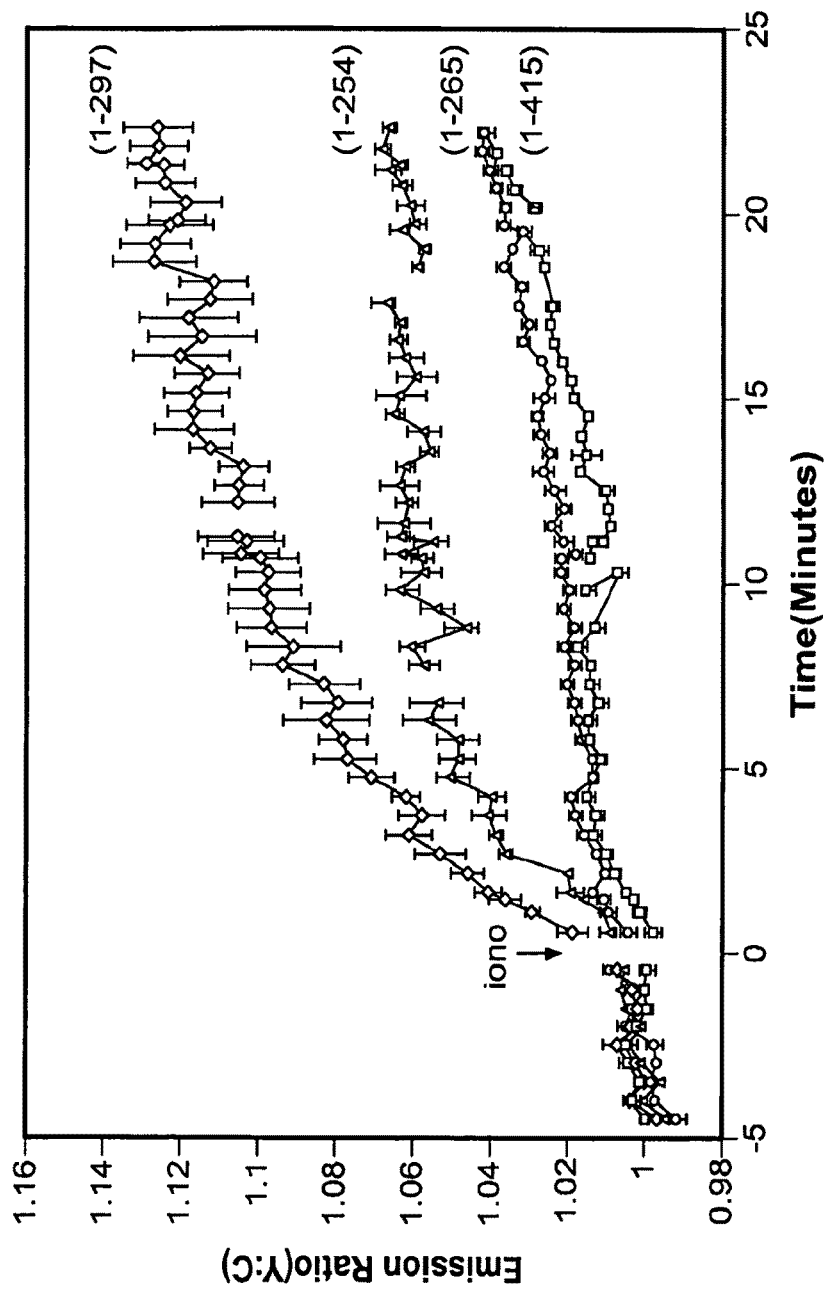
FIG. 26. Representative time courses of HeLa cells expressing various test constructs stimulated by ionomycin (1 µM). The emission ratio of each candidate construct was plotted as a function of time. The standard error for each time point is shown. Constructs were composed of either NFAT1 (1-415) (black squares, n=4), NFAT1(1-297) (light gray diamonds, n=2), NFAT1(1-265) (dark gray cross-hairs, n=2), or NFAT1(1-254) (light gray triangles, n=2) flanked by ECFP and cpV(L194) at the N- and C-terminus, respectively.

To generate a FRET-based reporter capable of monitoring calcineurin activity in live cells, we initially chose to flank NFAT1(1-415) with ECFP and cpV(L194) at the N- and C-termini, respectively. In response to $Ca^{2+}$ stimulation, the resulting construct exhibited an increase in its nuclear fluorescence intensity similar to that observed for ECFP-NFAT (1-415). However, this construct showed no change in FRET following $Ca^{2+}$ stimulation (FIG. 26). One interpretation of these results is that the calcineurin-mediated dephosphorylation induced conformational changes in NFAT1 are not translated into a FRET change because ECFP and cpV(L194) are not positioned appropriately. We therefore generated a series of truncations of the regulatory domain of NFAT1 while keeping the sites of conformational changes—located near the SRR-1 (residues 167-179) and the NLS (residues 249-253)—intact. Because the N-terminus of NFAT1 contains several docking sites known to recruit enzymes involved in the regulation of its phosphorylation state, we chose to truncate NFAT1 at its C-terminus, in the vicinity of the NLS. cpV(L194) was thus fused to NFAT1 at residues 254 (abutting the NLS), 265 (just prior to SP-3) and 297 (encompassing the SP-3 region) while ECFP remained fused to the extreme N-terminus of NFAT1 (FIG. 21). The emission ratio of yellow over cyan was then measured over time in HeLa cells expressing each construct, and their signals compared. While the construct containing NFAT1(1-265) responded to $Ca^{2+}$ influx in a manner similar to the original NFAT1(1-415)-containing species, the other two constructs were characterized by clearly detectable increases in their emission ratios following $Ca^{2+}$ stimulation (FIG. 21, FIG. 26). Of the four candidate reporters, the construct that contains NFAT1(1-297) showed the largest increase in its emission ratio following $Ca^{2+}$ stimulation (FIG. 22B) and is thus dubbed Calcineurin (CaN) Activity Reporter 1 (CaNAR1).

Figure 22:
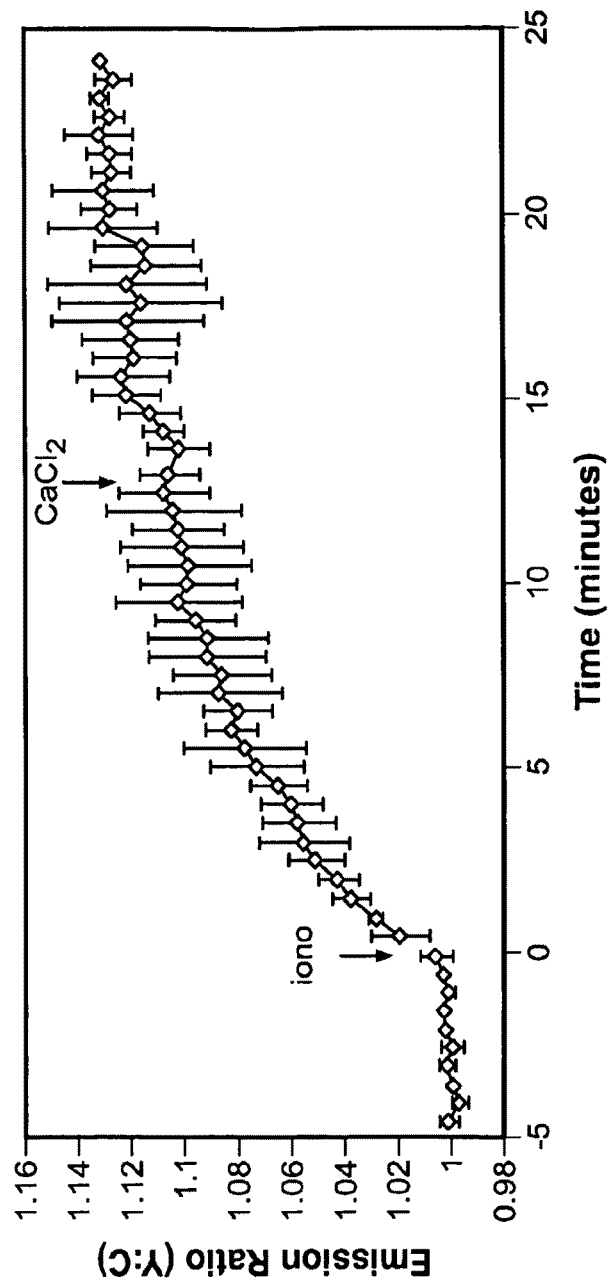
FIG. 22. Characterization of calcineurin activity reporter 1 (CaNAR1). Graph of representative response of CaNAR1-expressing HeLa cells following ionomycin treatment. Ionomycin (1 µM) and additional $CaCl_2$ (5 mM) were added to the imaging solution at the indicated times (arrows). The standard deviation for each time point is shown (n=2).
Figure 23A:
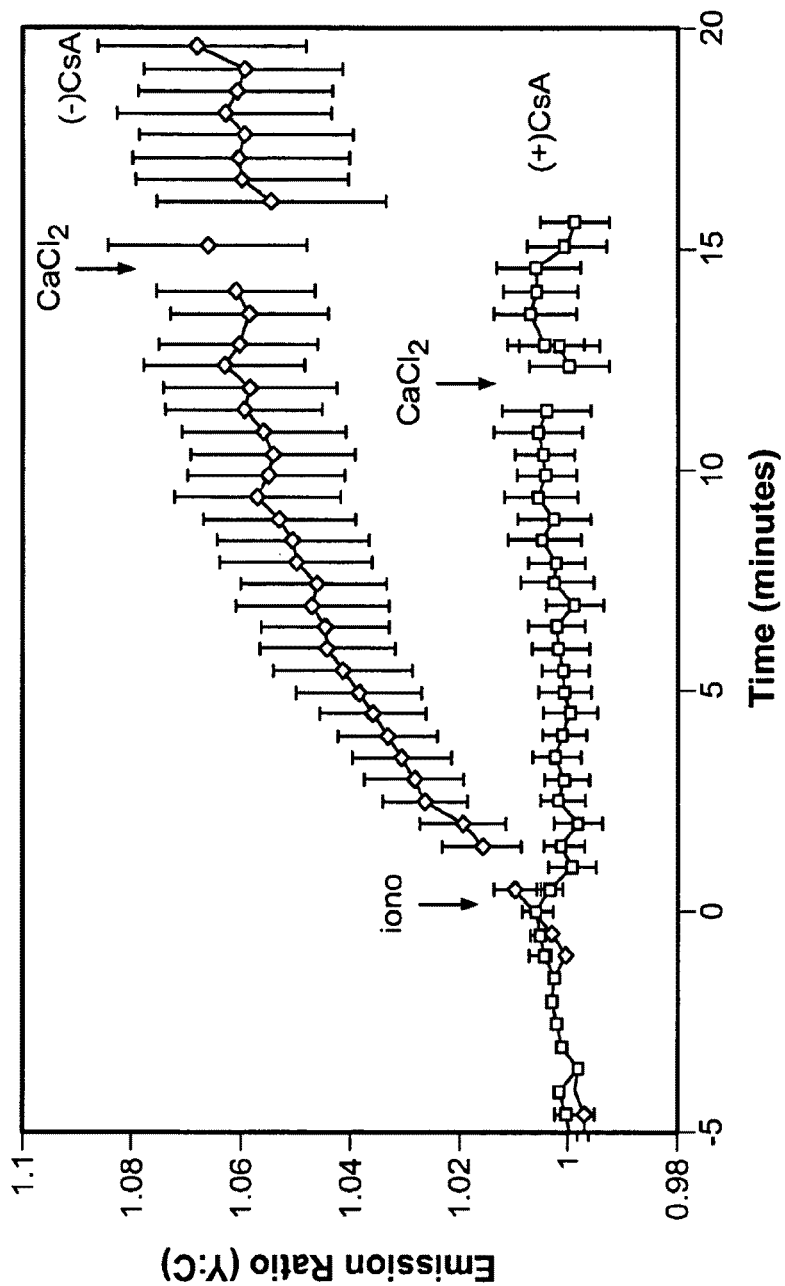
FIG. 23A-B. CaNAR1 is dephosphorylated in a calcineurin-dependent manner.

When expressed in HeLa cells, CaNAR1 is distributed primarily in the cytosol (FIG. 22A, first panel). After drug addition, this reporter exhibited an immediate increase in its emission ratio that continued to rise steadily for twelve minutes before reaching a maximum value of 6.3±1.5% ($t_{1/2}$=3.5 minutes) (FIGS. 22A and 23A). Once it had plateaued, the emission ratio remained constant for several minutes. A further increase in extracellular calcium did not induce a significant change in the emission ratio, suggesting that the maximum response had been achieved during this time. In contrast, removal of ionomycin from the imaging media resulted in a decrease in the emission ratio back to resting levels, consistent with previous studies showing that endogenous NFAT1 is rephosphorylated by cellular kinases shortly after ionomycin is removed from the culture medium.

Together, these data imply that $Ca^{2+}$ influx elicits a cellular response that converts CaNAR1 from an inactive (low FRET) to an active (high FRET) conformational state and that a new equilibrium between these two states is established shortly thereafter.

Though it is well-known that calcineurin dephosphorylates the regulatory domain of NFAT1 in a highly specific manner, we wanted to ensure that the increased emission ratio observed for CaNAR1 following $Ca^{2+}$ stimulation was indeed due to calcineurin-mediated dephosphorylation. Cyclosporin A (CsA) is a potent pharmacological inhibitor of calcineurin activity. Therefore, we examined the effects of CsA pretreatment on the ability of CaNAR1-expressing HeLa cells to respond to increases in $[Ca^{2+}]_i$. As shown in FIG. 23A, CsA completely abolished the FRET change induced by ionomycin, suggesting that the FRET changes observed for CaNAR1 result from calcineurin activity and not other $Ca^{2+}$-mediated processes.

Figure 23B:
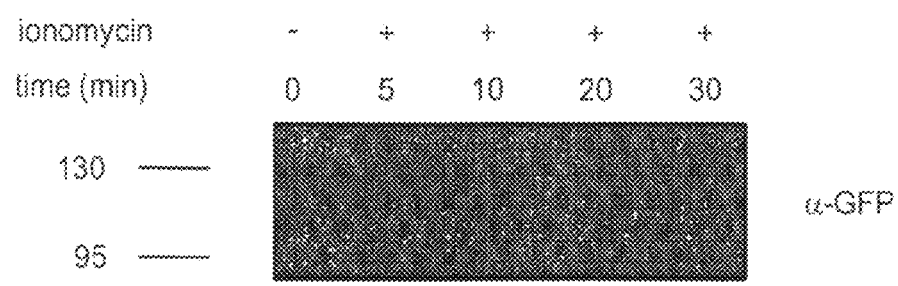

Next, to correlate the FRET change with dephosphorylation of CaNAR1, we took advantage of the fact that the electrophoretic mobility of NFAT1 is strongly influenced by its phosphorylation state. For example, previous studies have shown that NFAT1 molecules isolated from unstimulated cells migrate as a single band whose mobility is retarded relative to that of the unphosphorylated species. This behavior has been attributed to hyperphosphorylation of the regulatory domain. In contrast, $Ca^{2+}$-stimulated cells initially contain a collection of differentially-phosphorylated NFAT1 molecules that converge over time to migrate as a single, lower molecular weight species corresponding to the fully-dephosphorylated form of the protein. Therefore, we examined the electrophoretic mobility of CaNAR1 isolated from transiently-transfected HeLa cell lysates at various times after ionomycin treatment (FIG. 23B). Though its calculated molecular weight is 85 kDa, CaNAR1 migrated almost exclusively as an approximately 125 kDa species in uninduced cell lysates, consistent with hyperphosphorylation of its substrate region. However, five minutes after ionomycin treatment, the distribution of CaNAR1 became broader and less uniform, suggesting that a substantial portion of the reporter molecules had been dephosphorylated during this time period. Longer incubation times resulted in an increase in the mobility of nearly all of the CaNAR1 molecules. As expected, when cells were preincubated with CsA prior to ionomycin treatment, no change in the electrophoretic mobility of CaNAR1 was observed during the same period of time. Taken together, these data are consistent with the notion that CaNAR1 is progressively dephosphorylated by calcineurin in response to elevated $[Ca^{2+}]_i$. Thus, the observed FRET change is correlated with dephosphorylation of the reporter by calcineurin, providing a real-time readout for calcineurin activity.

Figure 24:
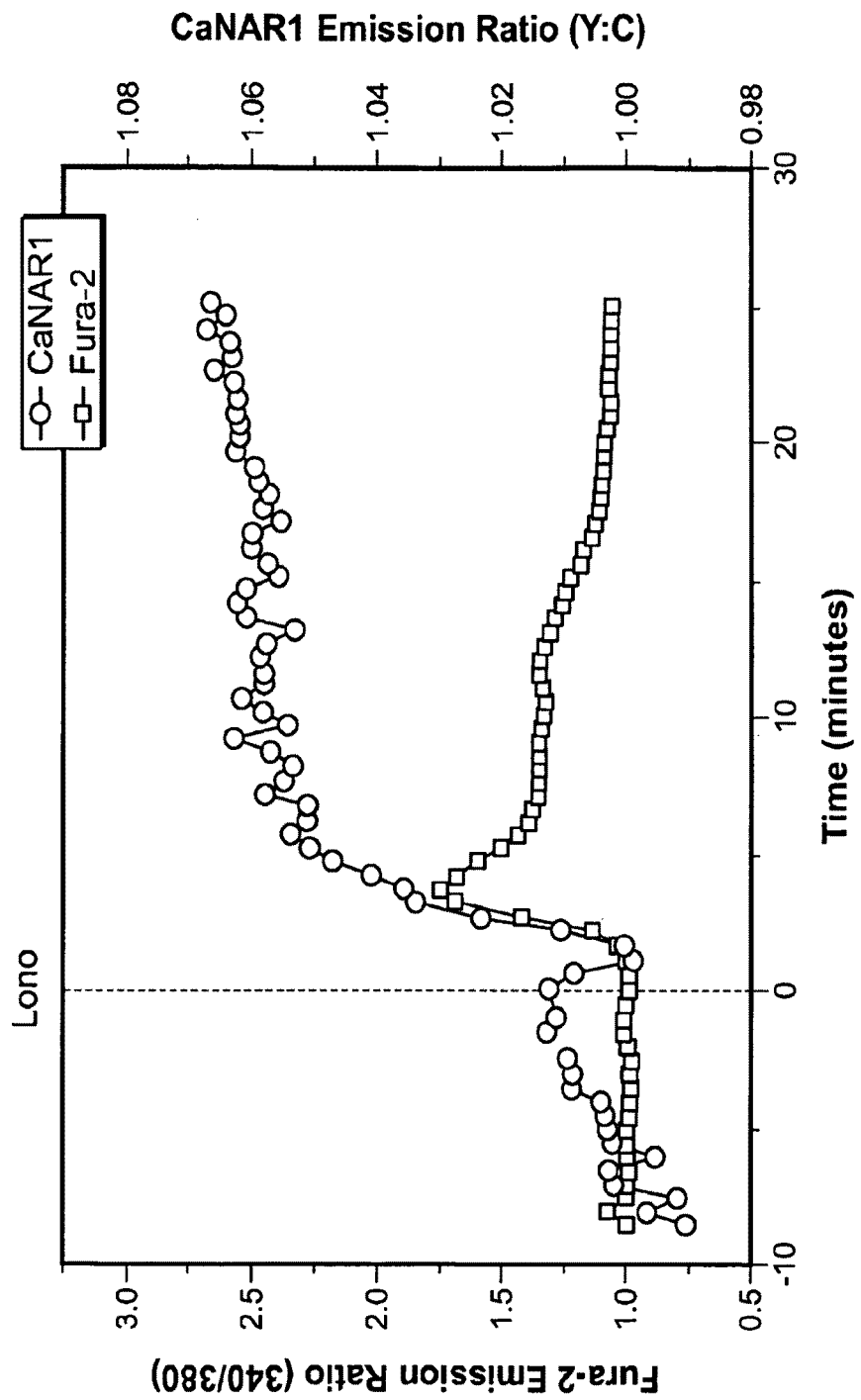
FIG. 24. Simultaneous measurement of $[Ca^{2+}]_i$ and calcineurin activity in a single cell. The emission ratios of CaNAR1 (black diamonds) and Fura-2 (open squares) were measured over time in response to ionomycin addition (1 µM, dotted line) in a single HeLa cell. A gray box indicates the period of time during which the apparent $[Ca^{2+}]_i$ had returned to basal levels following ionomycin-induced $Ca^{2+}$ stimulation. A representative response is shown.

To correlate the activation of calcineurin with $Ca^{2+}$ dynamics at the level of single cells, CaNAR1 and the $Ca^{2+}$ indicator, Fura-2, were used to simultaneously monitor changes in calcineurin activity and $[Ca^{2+}]_i$, respectively. As can be seen in FIG. 24, addition of ionomycin induced a rapid increase in $[Ca^{2+}]_i$ which led to the activation of calcineurin. No discernible lag was observed between $Ca^{2+}$ influx and calcineurin activation, suggesting that, in HeLa cells, calcineurin is activated seconds after $Ca^{2+}$ stimulation. Peak $Ca^{2+}$ concentrations were observed approximately 3.5 minutes after stimulation, at which time the emission ratio of CaNAR1 reached half-maximum (FIG. 24). Following an initial spike, the $Ca^{2+}$ concentration gradually decreased back to baseline levels. Interestingly, the emission ratio of CaNAR1 continued to increase during this period, suggesting that the reporter was being dephosphorylated by calcineurin even as the concentration of $Ca^{2+}$ decreased. Moreover, the emission ratio of CaNAR1 remained constant for several minutes after $[Ca^{2+}]_i$ had returned to near basal levels (FIG. 24, gray box), raising interesting mechanistic questions about the termination of calcineurin activity and the regulation of NFAT1. Future experiments will investigate termination of calcineurin activity under this and other cellular conditions.

Despite the relatively broad substrate specificity of most protein phosphatases, many cellular proteins are dephosphorylated in a highly-specific manner. Cells often achieve this feat by restricting the activity of protein phosphatases to distinct subcellular regions. Inside the cell, calcineurin is targeted to discrete microdomains where it is involved in the regulation of a diverse set of cellular processes. Thus, in addition to providing information about the timing of calcineurin activation, CaNAR1 may also be used to answer questions about the spatial regulation of calcineurin activity. Indeed, as a genetically-encoded and subcellularly targetable activity reporter, CaNAR1 represents a powerful tool for probing calcineurin activity in different subcellular regions and for monitoring specific pools of calcineurin within their endogenous environment.

The invention claimed is:

1. A phosphatase reporter, comprising:
 a donor moiety;
 a truncated form of a regulatory domain of NFAT1, wherein the truncated form is selected from the group consisting of amino acids 1-254 of NFAT1, amino acids 1-265 of NFAT1, and amino acids 1-297 of NFAT1, numbered according to SEQ ID NO:42, wherein the N terminus of the truncated form is conjugated to the donor moiety; and
 an acceptor moiety conjugated to the C terminus of the truncated form of the regulatory domain of NFAT1.

2. The phosphatase reporter of claim 1 which is a fusion protein.

3. A method of detecting an enzyme activity, comprising:
 detecting a first resonance energy transfer of the phosphatase reporter of claim 1 at a first time point;
 detecting a second resonance energy transfer of the phosphatase reporter at a second time point; and
 comparing the first and the second resonance energy transfers, wherein a difference between the first and the second resonance energy transfers reflects the enzyme activity.

4. The method of claim 3, wherein the phosphatase reporter is in a cell-free system.

5. The method of claim 3, wherein the phosphatase reporter is in a cell and wherein the cell is in vitro.

6. The method of claim 5, wherein the cell is in a well of a multi-well plate.

7. The method of claim 5, wherein each of a plurality of wells of the multi-well plate comprises a cell which comprises the phosphatase reporter.

8. The method of claim 3, wherein the first and second resonance energy transfers are detected using fluorescence activated cell sorting.

9. The phosphatase reporter of claim 1, wherein the donor moiety is enhanced cyan fluorescent protein.

10. The phosphatase reporter of claim 1, wherein the acceptor moiety is circularly-permuted yellow fluorescent protein Venus, cpV(L194).

11. The phosphatase reporter of claim 9, wherein the acceptor moiety is circularly-permuted yellow fluorescent protein Venus, cpV(L194).

12. The phosphatase reporter of claim 9, wherein the truncated form of the regulatory domain of NFAT1 consists of amino acids 1-254 of NFAT1.

13. The phosphatase reporter of claim 10, wherein the truncated form of the regulatory domain of NFAT1 consists of amino acids 1-254 of NFAT1.

14. The phosphatase reporter of claim 11, wherein the truncated form of the regulatory domain of NFAT1 consists of amino acids 1-254 of NFAT1.

15. The phosphatase reporter of claim 9, wherein the truncated form of the regulatory domain of NFAT 1 consists of amino acids 1-297 of NFAT 1.

16. The phosphatase reporter of claim 10, wherein the truncated form of the regulatory domain of NFAT 1 consists of amino acids 1-297 of NFAT 1.

17. The phosphatase reporter of claim 11, wherein the truncated form of the regulatory domain of NFAT 1 consists of amino acids 1-297 of NFAT 1.

18. The phosphatase reporter of claim 9, wherein the truncated form of the regulatory domain of NFAT 1 consists of amino acids 1-265 of NFAT 1.

19. The phosphatase reporter of claim 10, wherein the truncated form of the regulatory domain of NFAT 1 consists of amino acids 1-265 of NFAT 1.

20. The phosphatase reporter of claim 11, wherein the truncated form of the regulatory domain of NFAT 1 consists of amino acids 1-265 of NFAT 1.

21. The phosphatase reporter of claim 1, wherein the truncated form of the regulatory domain of NFAT1 consists of amino acids 1-254 of NFAT1.

22. The phosphatase reporter of claim 1, wherein the truncated form of the regulatory domain of NFAT 1 consists of amino acids 1-265 of NFAT 1.

23. The phosphatase reporter of claim 1, wherein the truncated form of the regulatory domain of NFAT 1 consists of amino acids 1-297 of NFAT 1.

* * * * *

SEQUENCE LISTING

```
<160> NUMBER OF SEQ ID NOS: 42

<210> SEQ ID NO 1
<211> LENGTH: 11
<212> TYPE: PRT
<213> ORGANISM: Artificial Sequence
<220> FEATURE:
<223> OTHER INFORMATION: nuclear localization signal

<400> SEQUENCE: 1

Pro Pro Lys Lys Lys Arg Lys Val Glu Asp Ala
1               5                   10

<210> SEQ ID NO 2
<211> LENGTH: 14
<212> TYPE: PRT
<213> ORGANISM: Artificial Sequence
<220> FEATURE:
<223> OTHER INFORMATION: plasma membrane targeting sequence
```

-continued

<400> SEQUENCE: 2

Pro Lys Lys Lys Lys Ser Lys Thr Lys Cys Val Ile Met
1               5                   10

<210> SEQ ID NO 3
<211> LENGTH: 31
<212> TYPE: PRT
<213> ORGANISM: Artificial Sequence
<220> FEATURE:
<223> OTHER INFORMATION: mitochondrial localization sequence

<400> SEQUENCE: 3

Pro Met Ala Ile Gln Leu Arg Ser Leu Phe Pro Leu Ala Leu Pro Gly
1               5                   10                  15

Met Leu Ala Leu Leu Gly Trp Trp Trp Phe Phe Ser Arg Lys Lys
            20                  25                  30

<210> SEQ ID NO 4
<211> LENGTH: 17
<212> TYPE: PRT
<213> ORGANISM: Artificial Sequence
<220> FEATURE:
<223> OTHER INFORMATION: mitochondrial matrix targeting signal

<400> SEQUENCE: 4

Pro Met Leu Ser Leu Arg Gly Ser Ile Arg Phe Phe Lys Arg Ser Gly
1               5                   10                  15

Ile

<210> SEQ ID NO 5
<211> LENGTH: 7
<212> TYPE: PRT
<213> ORGANISM: Artificial Sequence
<220> FEATURE:
<223> OTHER INFORMATION: tetracysteine motif
<221> NAME/KEY: VARIANT
<222> LOCATION: (1)...(7)
<223> OTHER INFORMATION: Xaa = Any Amino Acid
<221> NAME/KEY: VARIANT
<222> LOCATION: (1)...(7)
<223> OTHER INFORMATION: Xaa = Any Amino Acid
<221> NAME/KEY: VARIANT
<222> LOCATION: (1)...(7)
<223> OTHER INFORMATION: Xaa = Any Amino Acid

<400> SEQUENCE: 5

Pro Cys Cys Xaa Xaa Cys Cys
1               5

<210> SEQ ID NO 6
<211> LENGTH: 17
<212> TYPE: PRT
<213> ORGANISM: Artificial Sequence
<220> FEATURE:
<223> OTHER INFORMATION: linker

<400> SEQUENCE: 6

Pro Ala Gly Lys Pro Gly Ser Gly Glu Gly Ser Thr Lys Gly Leu Val
1               5                   10                  15

Asp

<210> SEQ ID NO 7
<211> LENGTH: 9
<212> TYPE: PRT
<213> ORGANISM: Artificial Sequence

```
<220> FEATURE:
<223> OTHER INFORMATION: linker

<400> SEQUENCE: 7

Pro Gly Gly Thr Gly Gly Ser Glu Leu
1               5

<210> SEQ ID NO 8
<211> LENGTH: 16
<212> TYPE: PRT
<213> ORGANISM: Artificial Sequence
<220> FEATURE:
<223> OTHER INFORMATION: FOXO1 Akt phosphorylation motif

<400> SEQUENCE: 8

Pro Pro Arg Pro Arg Ser Cys Thr Trp Pro Asp Pro Arg Pro Glu Phe
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Akt substrate

<400> SEQUENCE: 9

Pro Pro Phe Arg Gly Arg Ser Arg Thr Ala Pro Asp Asn Leu Trp Ala
1               5                   10                  15

<210> SEQ ID NO 10
<211> LENGTH: 12
<212> TYPE: PRT
<213> ORGANISM: Artificial Sequence
<220> FEATURE:
<223> OTHER INFORMATION: Akt substrate

<400> SEQUENCE: 10

Pro Arg Lys Arg Asp Arg Leu Gly Thr Leu Gly Asp
1               5                   10

<210> SEQ ID NO 11
<211> LENGTH: 21
<212> TYPE: PRT
<213> ORGANISM: Artificial Sequence
<220> FEATURE:
<223> OTHER INFORMATION: Erk substrate

<400> SEQUENCE: 11

Pro Arg Glu Leu Val Glu Pro Leu Thr Pro Ser Asp Glu Ala Pro Asn
1               5                   10                  15

Gln Ala Leu Leu Arg
            20

<210> SEQ ID NO 12
<211> LENGTH: 9
<212> TYPE: PRT
<213> ORGANISM: Artificial Sequence
<220> FEATURE:
<223> OTHER INFORMATION: linker

<400> SEQUENCE: 12

Pro Gly Thr Gly Gly Thr Ala Ala Ala
1               5

<210> SEQ ID NO 13
<211> LENGTH: 21
```

```
<212> TYPE: PRT
<213> ORGANISM: Artificial Sequence
<220> FEATURE:
<223> OTHER INFORMATION: docking sequence

<400> SEQUENCE: 13

Pro Pro Ile Glu Ser Ser Ile Leu Ala Gln Arg Arg Val Arg Lys Leu
1               5                   10                  15

Pro Ser Thr Thr Leu
            20

<210> SEQ ID NO 14
<211> LENGTH: 37
<212> TYPE: PRT
<213> ORGANISM: Artificial Sequence
<220> FEATURE:
<223> OTHER INFORMATION: linker-forkhead transcription factor-linker

<400> SEQUENCE: 14

Ser Ala Gly Lys Pro Gly Ser Gly Glu Gly Ser Thr Lys Gly Pro Arg
1               5                   10                  15

Pro Arg Ser Cys Thr Trp Pro Asp Pro Arg Pro Glu Phe Gly Gly Thr
            20                  25                  30

Gly Gly Ser Glu Leu
        35

<210> SEQ ID NO 15
<211> LENGTH: 37
<212> TYPE: PRT
<213> ORGANISM: Artificial Sequence
<220> FEATURE:
<223> OTHER INFORMATION: linker-Akt phosphorylation motif "BAD"-linker

<400> SEQUENCE: 15

Ser Ala Gly Lys Pro Gly Ser Gly Glu Gly Ser Thr Lys Gly Pro Phe
1               5                   10                  15

Pro Gly Arg Ser Arg Thr Ala Pro Asp Asn Leu Trp Ala Gly Gly Thr
            20                  25                  30

Gly Gly Ser Glu Leu
        35

<210> SEQ ID NO 16
<211> LENGTH: 33
<212> TYPE: PRT
<213> ORGANISM: Artificial Sequence
<220> FEATURE:
<223> OTHER INFORMATION: linker-Akt phosphorylation motif-linker

<400> SEQUENCE: 16

Ser Ala Gly Lys Pro Gly Ser Gly Glu Gly Ser Thr Lys Gly Arg Lys
1               5                   10                  15

Arg Asp Arg Leu Gly Thr Leu Gly Asp Gly Gly Thr Gly Gly Ser Glu
            20                  25                  30

Leu

<210> SEQ ID NO 17
<211> LENGTH: 20
<212> TYPE: PRT
<213> ORGANISM: Artificial Sequence
<220> FEATURE:
<223> OTHER INFORMATION: portion of MAPK activity reporter

<400> SEQUENCE: 17
```

-continued

```
Asp Val Ser Lys Thr Pro Glu Asp Glu Gly Asn Pro Leu Leu Glu Gln
1               5                   10                  15

Leu Glu Lys Lys
            20

<210> SEQ ID NO 18
<211> LENGTH: 14
<212> TYPE: PRT
<213> ORGANISM: Artificial Sequence
<220> FEATURE:
<223> OTHER INFORMATION: kinase substrate

<400> SEQUENCE: 18

Leu Arg Arg Ala Thr Leu Val Asp Gly Gly Thr Gly Gly Ser
1               5                   10

<210> SEQ ID NO 19
<211> LENGTH: 19
<212> TYPE: PRT
<213> ORGANISM: Artificial Sequence
<220> FEATURE:
<223> OTHER INFORMATION: kinase substrate

<400> SEQUENCE: 19

Arg Phe Arg Arg Phe Gln Thr Leu Asp Leu Ala Leu Ala Gly Gly Thr
1               5                   10                  15

Gly Gly Ser

<210> SEQ ID NO 20
<211> LENGTH: 14
<212> TYPE: PRT
<213> ORGANISM: Artificial Sequence
<220> FEATURE:
<223> OTHER INFORMATION: kinase substrate

<400> SEQUENCE: 20

Arg Phe Arg Arg Phe Gln Thr Leu Lys Ile Lys Ala Lys Ala
1               5                   10

<210> SEQ ID NO 21
<211> LENGTH: 25
<212> TYPE: PRT
<213> ORGANISM: Artificial Sequence
<220> FEATURE:
<223> OTHER INFORMATION: kinase substrate

<400> SEQUENCE: 21

Lys Lys Lys Lys Lys Arg Phe Ser Phe Lys Lys Ser Phe Lys Leu Ser
1               5                   10                  15

Gly Phe Ser Phe Lys Lys Asn Leu Leu
            20                  25

<210> SEQ ID NO 22
<211> LENGTH: 25
<212> TYPE: PRT
<213> ORGANISM: Artificial Sequence
<220> FEATURE:
<223> OTHER INFORMATION: kinase substrate

<400> SEQUENCE: 22

Lys Arg Phe Ser Ser Lys Lys Ser Phe Lys Leu Ser Gly Phe Ser Phe
1               5                   10                  15

Lys Lys Lys Lys Asn Lys Lys Glu Ala
            20                  25
```

```
<210> SEQ ID NO 23
<211> LENGTH: 24
<212> TYPE: PRT
<213> ORGANISM: Artificial Sequence
<220> FEATURE:
<223> OTHER INFORMATION: kinase substrate

<400> SEQUENCE: 23

Lys Arg Phe Ser Ser Lys Lys Ser Phe Lys Leu Ser Gly Phe Ser Phe
 1               5                  10                  15

Lys Lys Lys Ser Lys Lys Glu Ala
            20

<210> SEQ ID NO 24
<211> LENGTH: 17
<212> TYPE: PRT
<213> ORGANISM: Artificial Sequence
<220> FEATURE:
<223> OTHER INFORMATION: kinase substrate

<400> SEQUENCE: 24

Lys Lys Phe Ser Ser Lys Lys Pro Phe Lys Leu Ser Gly Phe Ser Phe
 1               5                  10                  15

Arg

<210> SEQ ID NO 25
<211> LENGTH: 23
<212> TYPE: PRT
<213> ORGANISM: Artificial Sequence
<220> FEATURE:
<223> OTHER INFORMATION: kinase substrate

<400> SEQUENCE: 25

Glu Thr Thr Ser Ser Phe Lys Lys Phe Phe Thr His Gly Thr Gly Phe
 1               5                  10                  15

Lys Lys Ser Lys Glu Asp Asp
            20

<210> SEQ ID NO 26
<211> LENGTH: 23
<212> TYPE: PRT
<213> ORGANISM: Artificial Sequence
<220> FEATURE:
<223> OTHER INFORMATION: kinase substrate

<400> SEQUENCE: 26

Lys Leu Phe Ser Ser Gly Leu Lys Lys Leu Ser Gly Lys Lys Gln
 1               5                  10                  15

Lys Gly Lys Arg Gly Gly Gly
            20

<210> SEQ ID NO 27
<211> LENGTH: 23
<212> TYPE: PRT
<213> ORGANISM: Artificial Sequence
<220> FEATURE:
<223> OTHER INFORMATION: kinase substrate

<400> SEQUENCE: 27

Glu Gly Ile Thr Pro Trp Ala Ser Phe Lys Lys Met Val Thr Pro Lys
 1               5                  10                  15

Lys Arg Val Arg Arg Pro Ser
            20
```

<210> SEQ ID NO 28
<211> LENGTH: 23
<212> TYPE: PRT
<213> ORGANISM: Artificial Sequence
<220> FEATURE:
<223> OTHER INFORMATION: kinase substrate

<400> SEQUENCE: 28

Glu Gly Val Ser Thr Trp Glu Ser Phe Lys Arg Leu Val Thr Pro Pro
1               5                   10                  15

Lys Lys Ser Lys Ser Lys Leu
            20

<210> SEQ ID NO 29
<211> LENGTH: 16
<212> TYPE: PRT
<213> ORGANISM: Artificial Sequence
<220> FEATURE:
<223> OTHER INFORMATION: Akt substrate

<400> SEQUENCE: 29

Ala Gly Lys Pro Gly Ser Gly Glu Gly Ser Thr Lys Gly Leu Val Asp
1               5                   10                  15

<210> SEQ ID NO 30
<211> LENGTH: 8
<212> TYPE: PRT
<213> ORGANISM: Artificial Sequence
<220> FEATURE:
<223> OTHER INFORMATION: LINKER

<400> SEQUENCE: 30

Gly Gly Thr Gly Gly Ser Glu Leu
1               5

<210> SEQ ID NO 31
<211> LENGTH: 10
<212> TYPE: PRT
<213> ORGANISM: Artificial Sequence
<220> FEATURE:
<223> OTHER INFORMATION: NUCLEAR LOCALIZATION SIGNAL

<400> SEQUENCE: 31

Pro Lys Lys Lys Arg Lys Val Glu Asp Ala
1               5                   10

<210> SEQ ID NO 32
<211> LENGTH: 15
<212> TYPE: PRT
<213> ORGANISM: Artificial Sequence
<220> FEATURE:
<223> OTHER INFORMATION: FOXO1 Akt phosphorylation motif

<400> SEQUENCE: 32

Pro Arg Pro Arg Ser Cys Thr Trp Pro Asp Pro Arg Pro Glu Phe
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Akt substrate

<400> SEQUENCE: 33

Pro Arg Phe Gly Arg Ser Arg Thr Ala Pro Asp Asn Leu Trp Ala

<210> SEQ ID NO 34
<211> LENGTH: 11
<212> TYPE: PRT
<213> ORGANISM: Artificial Sequence
<220> FEATURE:
<223> OTHER INFORMATION: Akt substrate

<400> SEQUENCE: 34

Arg Lys Arg Asp Arg Leu Gly Thr Leu Gly Asp
1               5                   10

<210> SEQ ID NO 35
<211> LENGTH: 78
<212> TYPE: DNA
<213> ORGANISM: Artificial Sequence
<220> FEATURE:
<223> OTHER INFORMATION: PRIMER

<400> SEQUENCE: 35
gagtcagaag gcaacccact gctcgagcag ctcgagaaga agggcggcac cggcggcagc      60
gagctcatgg tgagcaag                                                    78

<210> SEQ ID NO 36
<211> LENGTH: 59
<212> TYPE: DNA
<213> ORGANISM: Artificial Sequence
<220> FEATURE:
<223> OTHER INFORMATION: PRIMER

<400> SEQUENCE: 36
acgcgtcgac gacagtgtca agaccccga ggatgaaggc aacccactgc tcgagcagc        59

<210> SEQ ID NO 37
<211> LENGTH: 32
<212> TYPE: DNA
<213> ORGANISM: Artificial Sequence
<220> FEATURE:
<223> OTHER INFORMATION: PRIMER

<400> SEQUENCE: 37
ggcggattct tacttgtaca gctcgtccat gc                                    32

<210> SEQ ID NO 38
<211> LENGTH: 20
<212> TYPE: PRT
<213> ORGANISM: Artificial Sequence
<220> FEATURE:
<223> OTHER INFORMATION: Erk substrate

<400> SEQUENCE: 38

Arg Glu Leu Val Glu Pro Leu Thr Pro Ser Asp Glu Ala Pro Asn Gln
1               5                   10                  15

Ala Leu Leu Arg
            20

<210> SEQ ID NO 39
<211> LENGTH: 8
<212> TYPE: PRT
<213> ORGANISM: Artificial Sequence
<220> FEATURE:
<223> OTHER INFORMATION: linker

<400> SEQUENCE: 39

```
Gly Thr Gly Gly Thr Ala Ala Ala
  1               5
```

<210> SEQ ID NO 40
<211> LENGTH: 20
<212> TYPE: PRT
<213> ORGANISM: Artificial Sequence
<220> FEATURE:
<223> OTHER INFORMATION: RSK3gamma docking sequence

<400> SEQUENCE: 40

```
Pro Ile Glu Ser Ser Ile Leu Ala Gln Arg Arg Val Arg Lys Leu Pro
  1               5                  10                  15

Ser Thr Thr Leu
             20
```

<210> SEQ ID NO 41
<211> LENGTH: 48
<212> TYPE: PRT
<213> ORGANISM: Artificial Sequence
<220> FEATURE:
<223> OTHER INFORMATION: ERK reporter sequence

<400> SEQUENCE: 41

```
Arg Glu Leu Val Glu Pro Leu Thr Pro Ser Asp Glu Ala Pro Asn Gln
  1               5                  10                  15

Ala Leu Leu Arg Gly Thr Gly Gly Thr Ala Ala Ala Pro Ile Glu Ser
             20                  25                  30

Ser Ile Leu Ala Gln Arg Arg Val Arg Lys Leu Pro Ser Thr Thr Leu
         35                  40                  45
```

<210> SEQ ID NO 42
<211> LENGTH: 921
<212> TYPE: PRT
<213> ORGANISM: Homo sapiens

<400> SEQUENCE: 42

```
Met Asn Ala Pro Glu Arg Gln Pro Gln Pro Asp Gly Gly Asp Ala Pro
  1               5                  10                  15

Gly His Glu Pro Gly Gly Ser Pro Gln Asp Glu Leu Asp Phe Ser Ile
             20                  25                  30

Leu Phe Asp Tyr Glu Tyr Leu Asn Pro Asn Glu Glu Pro Asn Ala
         35                  40                  45

His Lys Val Ala Ser Pro Pro Ser Gly Pro Ala Tyr Pro Asp Asp Val
     50                  55                  60

Met Asp Tyr Gly Leu Lys Pro Tyr Ser Pro Leu Ala Ser Leu Ser Gly
 65                  70                  75                  80

Glu Pro Pro Gly Arg Phe Gly Glu Pro Asp Arg Val Gly Pro Gln Lys
                 85                  90                  95

Phe Leu Ser Ala Ala Lys Pro Ala Gly Ala Ser Gly Leu Ser Pro Arg
            100                 105                 110

Ile Glu Ile Thr Pro Ser His Glu Leu Ile Gln Ala Val Gly Pro Leu
        115                 120                 125

Arg Met Arg Asp Ala Gly Leu Leu Val Glu Gln Pro Pro Leu Ala Gly
    130                 135                 140

Val Ala Ala Ser Pro Arg Phe Thr Leu Pro Val Pro Gly Phe Glu Gly
145                 150                 155                 160

Tyr Arg Glu Pro Leu Cys Leu Ser Pro Ala Ser Ser Gly Ser Ser Ala
                165                 170                 175
```

```
Ser Phe Ile Ser Asp Thr Phe Ser Pro Tyr Thr Ser Pro Cys Val Ser
            180                 185                 190

Pro Asn Asn Gly Gly Pro Asp Asp Leu Cys Pro Gln Phe Gln Asn Ile
        195                 200                 205

Pro Ala His Tyr Ser Pro Arg Thr Ser Pro Ile Met Ser Pro Arg Thr
    210                 215                 220

Ser Leu Ala Glu Asp Ser Cys Leu Gly Arg His Ser Pro Val Pro Arg
225                 230                 235                 240

Pro Ala Ser Arg Ser Ser Pro Gly Ala Lys Arg Arg His Ser Cys
                245                 250                 255

Ala Glu Ala Leu Val Ala Leu Pro Pro Gly Ala Ser Pro Gln Arg Ser
            260                 265                 270

Arg Ser Pro Ser Pro Gln Pro Ser Ser His Val Ala Pro Gln Asp His
        275                 280                 285

Gly Ser Pro Ala Gly Tyr Pro Pro Val Ala Gly Ser Ala Val Ile Met
    290                 295                 300

Asp Ala Leu Asn Ser Leu Ala Thr Asp Ser Pro Cys Gly Ile Pro Pro
305                 310                 315                 320

Lys Met Trp Lys Thr Ser Pro Asp Pro Ser Pro Val Ser Ala Ala Pro
                325                 330                 335

Ser Lys Ala Gly Leu Pro Arg His Ile Tyr Pro Ala Val Glu Phe Leu
            340                 345                 350

Gly Pro Cys Glu Gln Gly Glu Arg Arg Asn Ser Ala Pro Glu Ser Ile
        355                 360                 365

Leu Leu Val Pro Pro Thr Trp Pro Lys Pro Leu Val Pro Ala Ile Pro
    370                 375                 380

Ile Cys Ser Ile Pro Val Thr Ala Ser Leu Pro Pro Leu Glu Trp Pro
385                 390                 395                 400

Leu Ser Ser Gln Ser Gly Ser Tyr Glu Leu Arg Ile Glu Val Gln Pro
                405                 410                 415

Lys Pro His His Arg Ala His Tyr Glu Thr Glu Gly Ser Arg Gly Ala
            420                 425                 430

Val Lys Ala Pro Thr Gly Gly His Pro Val Val Gln Leu His Gly Tyr
        435                 440                 445

Met Glu Asn Lys Pro Leu Gly Leu Gln Ile Phe Ile Gly Thr Ala Asp
    450                 455                 460

Glu Arg Ile Leu Lys Pro His Ala Phe Tyr Gln Val His Arg Ile Thr
465                 470                 475                 480

Gly Lys Thr Val Thr Thr Thr Ser Tyr Glu Lys Ile Val Gly Asn Thr
                485                 490                 495

Lys Val Leu Glu Ile Pro Leu Glu Pro Lys Asn Asn Met Arg Ala Thr
            500                 505                 510

Ile Asp Cys Ala Gly Ile Leu Lys Leu Arg Asn Ala Asp Ile Glu Leu
        515                 520                 525

Arg Lys Gly Glu Thr Asp Ile Gly Arg Lys Asn Thr Arg Val Arg Leu
    530                 535                 540

Val Phe Arg Val His Ile Pro Glu Ser Ser Gly Arg Ile Val Ser Leu
545                 550                 555                 560

Gln Thr Ala Ser Asn Pro Ile Glu Cys Ser Gln Arg Ser Ala His Glu
                565                 570                 575

Leu Pro Met Val Glu Arg Gln Asp Thr Asp Ser Cys Leu Val Tyr Gly
            580                 585                 590

Gly Gln Gln Met Ile Leu Thr Gly Gln Asn Phe Thr Ser Glu Ser Lys
```

-continued

```
            595                 600                 605
Val Val Phe Thr Glu Lys Thr Thr Asp Gly Gln Gln Ile Trp Glu Met
        610                 615                 620

Glu Ala Thr Val Asp Lys Asp Lys Ser Gln Pro Asn Met Leu Phe Val
625                 630                 635                 640

Glu Ile Pro Glu Tyr Arg Asn Lys His Ile Arg Thr Pro Val Lys Val
                645                 650                 655

Asn Phe Tyr Val Ile Asn Gly Lys Arg Lys Arg Ser Gln Pro Gln His
            660                 665                 670

Phe Thr Tyr His Pro Val Pro Ala Ile Lys Thr Glu Pro Thr Asp Glu
        675                 680                 685

Tyr Asp Pro Thr Leu Ile Cys Ser Pro Thr His Gly Gly Leu Gly Ser
    690                 695                 700

Gln Pro Tyr Tyr Pro Gln His Pro Met Val Ala Glu Ser Pro Ser Cys
705                 710                 715                 720

Leu Val Ala Thr Met Ala Pro Cys Gln Gln Phe Arg Thr Gly Leu Ser
                725                 730                 735

Ser Pro Asp Ala Arg Tyr Gln Gln Gln Asn Pro Ala Ala Val Leu Tyr
            740                 745                 750

Gln Arg Ser Lys Ser Leu Ser Pro Ser Leu Leu Gly Tyr Gln Gln Pro
        755                 760                 765

Ala Leu Met Ala Ala Pro Leu Ser Leu Ala Asp Ala His Arg Ser Val
    770                 775                 780

Leu Val His Ala Gly Ser Gln Gly Gln Ser Ser Ala Leu Leu His Pro
785                 790                 795                 800

Ser Pro Thr Asn Gln Gln Ala Ser Pro Val Ile His Tyr Ser Pro Thr
                805                 810                 815

Asn Gln Gln Leu Arg Cys Gly Ser His Gln Glu Phe Gln His Ile Met
            820                 825                 830

Tyr Cys Glu Asn Phe Ala Pro Gly Thr Thr Arg Pro Gly Pro Pro Pro
        835                 840                 845

Val Ser Gln Gly Gln Arg Leu Ser Pro Gly Ser Tyr Pro Thr Val Ile
    850                 855                 860

Gln Gln Gln Asn Ala Thr Ser Gln Arg Ala Ala Lys Asn Gly Pro Pro
865                 870                 875                 880

Val Ser Asp Gln Lys Glu Val Leu Pro Ala Gly Val Thr Ile Lys Gln
                885                 890                 895

Glu Gln Asn Leu Asp Gln Thr Tyr Leu Asp Asp Glu Leu Ile Asp Thr
            900                 905                 910

His Leu Ser Trp Ile Gln Asn Ile Leu
        915                 920
```